United States Patent
He et al.

(10) Patent No.: US 12,382,953 B2
(45) Date of Patent: Aug. 12, 2025

(54) SYSTEM, DEVICE, AND METHOD FOR CELL CRYOPRESERVATION VIA SAND-MEDIATED ICE SEEDING

(71) Applicant: University of Maryland, College Park, College Park, MD (US)

(72) Inventors: Xiaoming He, Bethesda, MD (US); Weijie Li, Shanghai (CN); Bin Jiang, College Park, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 17/659,432

(22) Filed: Apr. 15, 2022

(65) Prior Publication Data
US 2022/0330544 A1 Oct. 20, 2022

Related U.S. Application Data

(60) Provisional application No. 63/176,212, filed on Apr. 16, 2021.

(51) Int. Cl.
| | |
|---|---|
| A01N 1/02 | (2006.01) |
| A01N 1/125 | (2025.01) |
| A01N 1/147 | (2025.01) |
| A01N 1/162 | (2025.01) |
| C12N 5/074 | (2010.01) |

(52) U.S. Cl.
CPC ............. *A01N 1/162* (2025.01); *A01N 1/125* (2025.01); *A01N 1/147* (2025.01); *C12N 5/0696* (2013.01)

(58) Field of Classification Search
CPC .. A01N 1/0284; A01N 1/0221; A01N 1/0268; C12N 5/0696
See application file for complete search history.

(56) References Cited

U.S. PATENT DOCUMENTS 10,015,958 B2 * 7/2018 Murray ................ A01N 1/0268

OTHER PUBLICATIONS

Li et al. Front. Bioeng. Biotechnol. 2020; 8:1. doi: 10.3389/fbioe.2020.00001. p. 1-13. (Year: 2020).*
Yoshie et al., Biophysical Journal. 2018; 114: 2194-2199. (Year: 2018).*
Li et al., On-chip direct freezing and thawing of mammalian cells. RSC Adv., 2014, 4, 34443-34447. (Year: 2014).*
López et al., "Chemically Defined, Clinical-Grade Cryopreservation of Human Adipose Stem Cells", Methods in Molecular Biology, vol. 2180, pp. 555-567, 2021.
Singh et al., "Induced pluripotent stem cells: applications in regenerative medicine, disease modeling, and drug discovery", Frontiers In Cell and Development Biology, vol. 3, Article 2, pp. 1-18, Feb. 2015.
Stensvaag et al., "Cryopreservation of Alginate-Encapsulated Recombinant Cells for Antiangiogenic Therapy", Cell Transplantation, vol. 13, pp. 35-44, 2004.
Stewart et al., "Intracellular Delivery of Trehalose for Cell Banking", Langmuir, vol. 35, No. 23, pp. 7414-7422, Jun. 2019.
Theunissen et al., "Systematic Identification of Culture Conditions for Induction and Maintenance of Naive Human Pluripotency", Cell Stem Cell, vol. 15, pp. 1-17, Oct. 2014.
Trad et al., "Effects of cryoprotectants and ice-seeding temperature on intracellular freezing and survival of human oocytes", Human Reproduction, vol. 14, No. 6, pp. 1569-1577, 1998.
Verheijen et al., "DMSO induces drastic changes in human cellular processes and epigenetic landscape in vitro", Scientific Reports, vol. 9, No. 4641, pp. 1-12, 2019.
Wang et al., "Magnetic induction heating of superparamagnetic nanoparticles during rewarming augments the recovery of hUCM-MSCs cryopreserved by vitrification", Acta Biomater., vol. 33, pp. 264-274, Mar. 2016.
Wang et al., "Generation of clinical-grade human induced pluripotent stem cells in Xeno-free conditions", Stem Cell Research & Therapy, vol. 6, No. 223, pp. 1-11, 2015.
Weng et al., "Dimethyl sulfoxide-free cryopreservation for cell therapy: A review", Cryobiology, pp. 1-9, 2020.
Xu et al., "Biomaterials for stem cell engineering and biomanufacturing", Bioactive Materials, vol. 4, pp. 366-379, 2019.
Yu et al., "Induced Pluripotent Stem Cell Lines Derived from Human Somatic Cells", Science, vol. 318, pp. 1917-1920, Dec. 2007.
Yuan et al., "Efficient long-term cryopreservation of pluripotent stem cells at -80 °C", Scientific Reports, vol. 6, No. 34476, pp. 1-13, 2016.
Zavos et al., "Effects of Various Degrees of Supercooling and Nucleation Temperatures on Fertility of Frozen Turkey Spermatozoa1", Cryobiology, vol. 20, pp. 553-559, 1983.

(Continued)

*Primary Examiner* — Laura Schuberg
*Assistant Examiner* — Jianjian Zhu
(74) *Attorney, Agent, or Firm* — McKee, Voorhees & Sease, PLC

(57) ABSTRACT

Human induced pluripotent stem cells (hiPSCs) possess tremendous potential for tissue regeneration and banking hiPSCs by cryopreservation for their ready availability is crucial to their widespread use. However, contemporary methods for hiPSC cryopreservation are associated with both limited cell survival and high concentration of toxic cryoprotectants and/or serum. The latter may cause spontaneous differentiation and introduce xenogeneic factors, which may compromise the quality of hiPSCs. Here, sand from nature is discovered to be capable of seeding ice above −10° C., which enables cryopreservation of hiPSCs with no serum, minimized cryoprotectant, and high cell survival. Furthermore, the cryopreserved hiPSCs retain high pluripotency and functions judged by the pluripotency marker expression, cell cycle analysis, and capability of differentiation into the three germ layers. This unique sand-mediated cryopreservation method may greatly facilitate the convenient and ready availability of high-quality hiPSCs and probably many other types of cells/tissues for the emerging cell-based translational medicine.

17 Claims, 14 Drawing Sheets

(56) References Cited

OTHER PUBLICATIONS

Zhang et al., "Preferential vitrification of water in small alginate microcapsules significantly augments cell cryopreservation by vitrification", Biomed Microdevices, vol. 12, pp. 89-96, 2010.

Zhang et al., "Cold-Responsive Nanoparticle Enables Intracellular Delivery and Rapid Release of Trehalose for Organic-Solvent-Free Cryopreservation", Nano Letters, vol. 19, pp. 9051-9061, 2019.

Zhao et al., "Hydrogel Encapsulation Facilitates Rapid-Cooling Cryopreservation of Stem Cell-Laden Core-Shell Microcapsules as Cell-Biomaterial Constructs", Advanced Healthcare Materials, 1700988, pp. 1-13, 2017.

Jin et al., "Intracellular ice formation in mouse zygotes and early morulae vs. cooling rate and temperature-experimental vs. theory", Cryobiology, pp. 1-6, 2016.

Bueno et al., "The Rock Inhibitor Y-27632 Negatively Affects the Expansion/Survival of Both Fresh and Cryopreserved Cord Blood-Derived CD34+ Hematopoietic Progenitor Cells", Stem Cell Rev and Rep, vol. 6, pp. 215-223, 2010.

Cao et al., "The Unusual Properties of Polytetrafluoroethylene Enable Massive-Volume Vitrification of Stem Cells with Low-Concentration Cryoprotectants", Adv. Mater. Technol., 1800289, pp. 1-14, 2018.

Chambers et al. "Highly efficient neural conversion of human ES and iPS cells by dual inhibition of SMAD signaling", Nature Biotechnology, vol. 27, No. 3, pp. 275-281, 2009.

Chetty et al., "A simple tool to improve pluripotent stem cell differentiation", Nature Methods, pp. 1-6, 2013.

Cox et al. "Historical perspectives and the future of adverse reactions associated with haemopoietic stem cells cryopreserved with dimethyl sulfoxide", Cell Tissue Bank, vol. 13, pp. 203-215, 2012.

Crowe et al., "Preservation of mammalian cells-learning nature's tricks", Nature Biotechnology, vol. 18, pp. 145-146, Feb. 2000.

Damjanov et al., "Teratomas produced from human pluripotent stem cells xenografted into immunodeficient mice—a histopathology atlas", Int. J. Dev. Biol., vol. 60, pp. 337-419, 2016.

Diller, Kenneth R., "Quantitative low temperature optical microscopy of biological systems", Journal of Microscopy, vol. 126, Pt. 1, pp. 9-28, Apr. 1982.

Eroglu et al., "Intracellular trehalose improves the survival of cryopreserved mammalian cells", Nature Biotechnology, vol. 18, pp. 163-167, Feb. 2000.

Franks, Felix, "Biophysics and Biochemistry at Low Temperatures", FEBS Letters, vol. 220, No. 2, 1 page, Aug. 1987.

Gläfke et al., "Cryopreservation of Platelets Using Trehalose: The Role of Membrane Phase Behavior During Freezing", Biotechnology Progress, vol. 28, No. 5, pp. 1-8, 2012.

Grein et al., "Alternatives to dimethylsulfoxide for serum-free cryopreservation of human mesenchymal stem cells", Int J Artif Organs, vol. 33, No. 6, pp. 370-380, 2010.

Harrison et al., "The ice-nucleating ability of quartz immersed in water and its atmospheric importance compared to K-feldspar", Atmos. Chem. Phys., vol. 19, pp. 11343-11361, 2019.

He et al., "Quantification of Temperature and Injury Response in Thermal Therapy and Cryosurgery", Critical Reviews In Biomedical Engineering, vol. 31, (5 & 6), pp. 355-421, 2003.

He, Xiaoming, "Thermostability of Biological Systems: Fundamentals, Challenges, and Quantification", The Open Biomedical Engineering Journal, vol. 5, pp. 47-73, 2011.

Hentze et al., "Teratoma formation by human embryonic stem cells: Evaluation of essential parameters for future safety studies", Stem Cell Research, vol. 2, pp. 198-210, 2009.

Holden et al., "High-speed imaging of ice nucleation in water proves the existence of active sites", Science Advances, vol. 5, eaav4316, pp. 1-10, Feb. 2019.

Huang et al., "Alginate Hydrogel Microencapsulation Inhibits Devitrification and Enables Large-Volume Low-CPA Cell Vitrification", Adv. Funct. Mater., vol. 25, pp. 6839-6850, 2015.

Huang et al., "Predehydration and Ice Seeding in the Presence of Trehalose Enable Cell Cryopreservation", ACS Biomater. Sci. Eng., vol. 3, pp. 1758-1768, 2017.

Huang et al., "Human iPSC banking: barriers and opportunities", Journal of Biomedical Science, vol. 26, No. 87, pp. 1-14, 2019.

Hunt, Charles J., "Technical Considerations in the Freezing, Low-Temperature Storage and Thawing of Stem Cells for Cellular Therapies", Transfus Med Hemother, vol. 46, pp. 134-149, 2019.

Imaizumi et al., "A Simple and Highly Effective Method for Slow-Freezing Human Pluripotent Stem Cells Using Dimethyl Sulfoxide, Hydroxyethyl Starch and Ethylene Glycol", PLoS One, vol. 9, Issue 2, e88696, pp. 1-11, Feb. 2014.

Isachenko, Dr. Vladimir, "Cryopreservation of human ovarian tissue: effect of spontaneous and initiated ice formation", Reproductive BioMedicine Online, vol. 16, No. 3, pp. 336-345, 2008.

Jiang et al., "Heart regeneration with human pluripotent stem cells: Prospects and challenges", Bioactive Materials, vol. 5, pp. 74-81, 2020.

Jiang et al., "Generation of cardiac spheres from primate pluripotent stem cells in a small molecule-based 3D system", Biomaterials, vol. 65, pp. 103-114, 2015.

Jiang et al., "Sand-mediated ice seeding enables serum-free low-cryoprote cryopreservation of human induced pluripotent stem cells", Bioactive Materials, vol. 6, pp. 4377-4388, 2021.

Jiang et al., "Stem Cell Therapy of Myocardial Infarction: A Promising Opportunity in Bioengineering", Advanced Therapeutics, 1900182, pp. 1-24, 2020.

Kleinhans, F. W., "Review—Membrane Permeability Modeling: Kedem-Katchalsky vs a Two-Parameter Formalism", Cryobiology, vol. 37, pp. 271-289, 1998.

Kojima et al., "Effect of Silver Iodide as an Ice Inducer on Viability of Frozen-Thawed Rabbit Morulae", Theriogenology, vol. 26, No. 3, pp. 341-352, Sep. 1986.

Kojima et al., "Effect of Ice Nucleation by Droplet of Immobilized Silver Iodide on Freezing of Rabbit and Bovine Embryos", Theriogenology, vol. 30, No. 6, pp. 1199-1207, Dec. 1988.

Kumar et al., "Ice nucleation activity of silicates and aluminosilicates in pure water and aqueous solutions—Part 2: Quartz and amorphous silica", Atmos. Chem. Phys., vol. 19, pp. 6035-6058, 2019.

Lee et al., "Derivation of neural crest cells from human pluripotent stem cells", Nature Protocols, vol. 5, No. 4, pp. 688-701, 2010.

Li et al., "Comparison of three methods for cryopreservation of human embryonic stem cells", Fertility and Sterility, vol. 93, No. 3, pp. 999-1005, Feb. 2010.

Liu et al., "Dual Suppression Effect of Magnetic Induction Heating and Microencapsulation on Ice Crystallization Enables Low-Cryoprotectant Vitrification of Stem Cell-Alginate hydrogel Constructs", ACS Appl Mater Interfaces, vol. 10, No. 19, pp. 16822-16835, May 2018.

Liu et al., "Cryopreservation of Human Pluripotent Stem Cells in Defined Medium", Current Protocols in Stem Cell Biology, 1C.17.1-1C.17.13, pp. 1-13, Nov. 2014.

Maki et al., "Ice Nucleation Induced by Pseudomonas syringae1", Applied Microbiology, pp. 456-459, Sep. 1974.

Manuchehrabadi et al., "Improved tissue cryopreservation using inductive heating of magnetic nanoparticles", Science Translational Medicine, vol. 9, eaah4586, pp. 1-10, Mar. 2017.

Massie et al., "Cryopreservation of Encapsulated Liver Spheroids for a Bioartificial Liver: Reducing Latent Cryoinjury Using an Ice Nucleating Agent", Tissue Engineering: Part C, vol. 17, No. 7, pp. 765-774, 2011.

Massie et al., "GMP Cryopreservation of Large Volumes of Cells for Regenerative Medicine: Active Control of the Freezing Process", Tissue Engineering: Part C, vol. 20, No. 9, pp. 693-702, 2014.

Mastromonaco et al., "Somatic Cells, Stem Cells, and Induced Pluripotent Stem Cells: How Do They Now Contribute to Conservation?", Advances in Experimental Medicine and Biology, vol. 753, pp. 385-427, 2014.

Mazur, Peter, "Physical and Temporal Factors Involved in the Death of Yeast at Subzero Temperatures", Biophysical Journal, vol. 1, pp. 247-264, 1961.

(56) References Cited

OTHER PUBLICATIONS

Mazur, Peter, "Freezing of living cells: mechanisms and implications", American Journal of Physiology-Cell Physiology, vol. 247, No. 3, pp. C125-C142, 1984.
Miyamoto et al., "Cryopreservation of Induced Pluripotent Stem Cells", Cell Medicine, vol. 3, pp. 89-95, 2012.
Miyazaki et al., "Slow Cooling Cryopreservation Optimized to Human Pluripotent Stem Cells", Adv Exp Med Biol., vol. 951, pp. 57-65, 2016.
Morizane et al., "Small-Molecule Inhibitors of Bone Morphogenic Protein and Activin/Nodal Signals Promote Highly Efficient Neural Induction From Human Pluripotent Stem Cells", Journal of Neuroscience Research, vol. 89, pp. 117-126, 2011.
Morris et al., "Ice nucleation active bacteria and their potential role in precipitation", J. Phys. IV France, vol. 121, pp. 87-103, 2004.
Morris et al., "Controlled ice nucleation in cryopreservation—A review", Cryobiology, vol. 66, pp. 85-92, 2013.
Otsuji et al., "A 3D Sphere Culture System Containing Functional Polymers for Large-Scale Human Pluripotent Stem Cell Production", Stem Cell Reports, vol. 2, pp. 734-745, May 2014.
Rao et al., "Nanoparticle-Mediated Intracellular Delivery Enables Cryopreservation of Human Adipose-Derived Stem Cells Using Trehalose as the Sole Cryoprotectant", ACS Appl Mater Interfaces, vol. 7, No. 8, pp. 5017-5028, Mar. 2015.
Rowley et al., "Effect of DMSO exposure without cryopreservation on hematopoietic progenitor cells", Bone Marrow Transplantation, vol. 11, pp. 389-393, 1993.

* cited by examiner

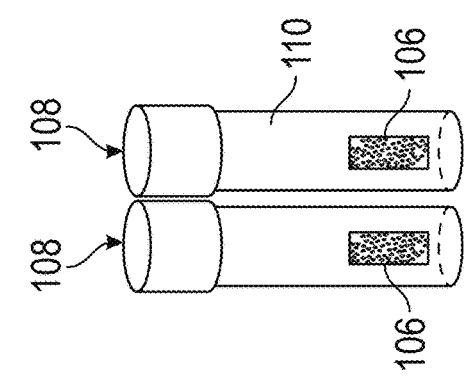
FIG. 1A
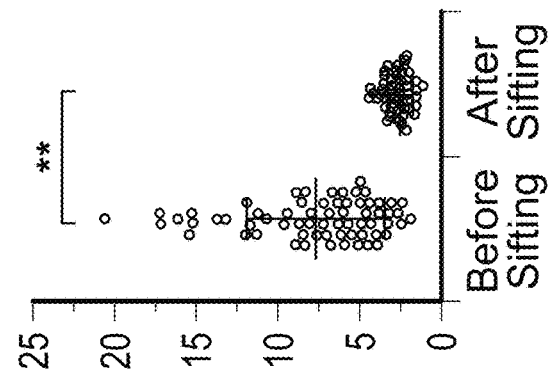
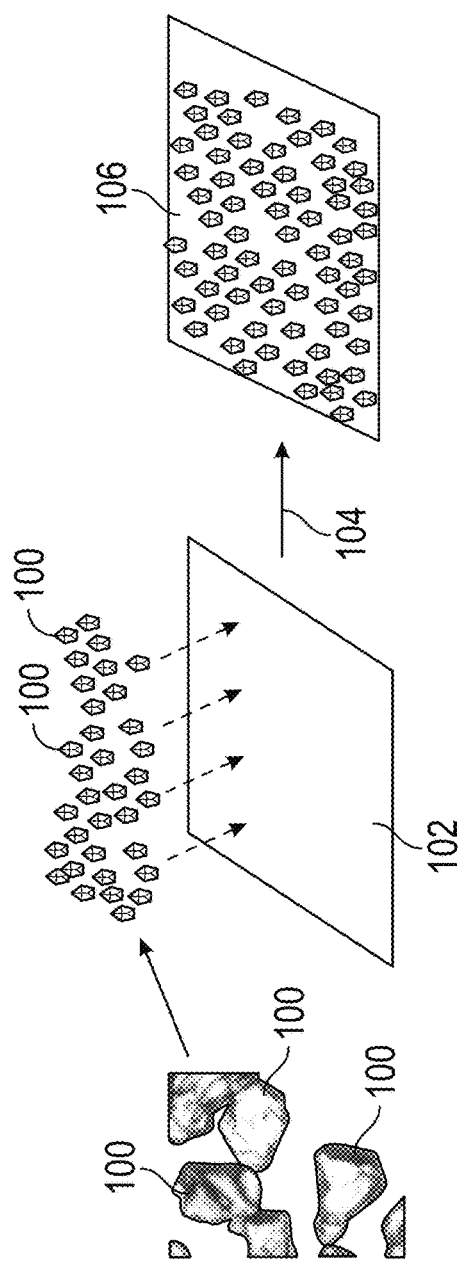
FIG. 1B
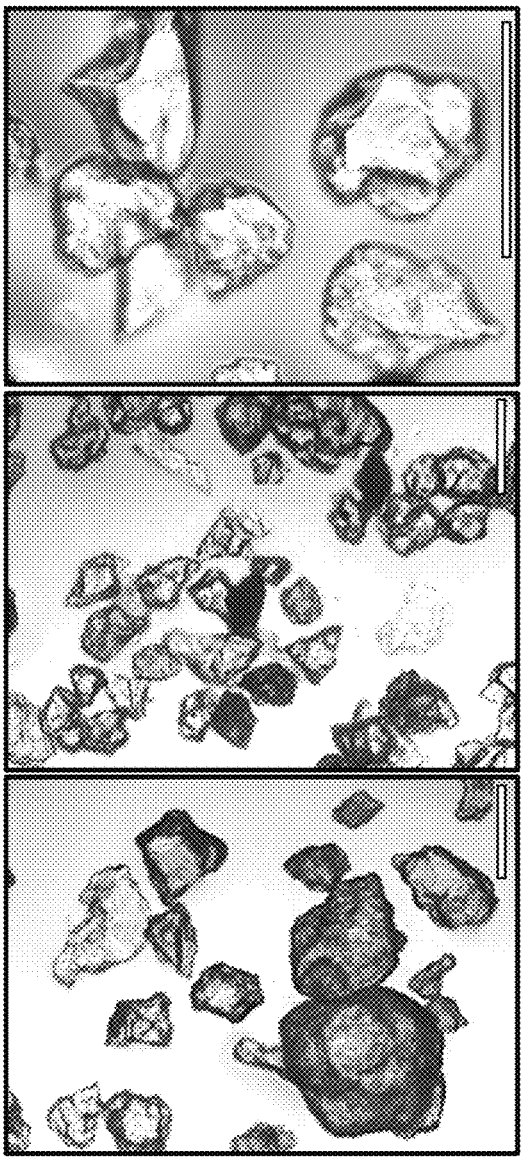

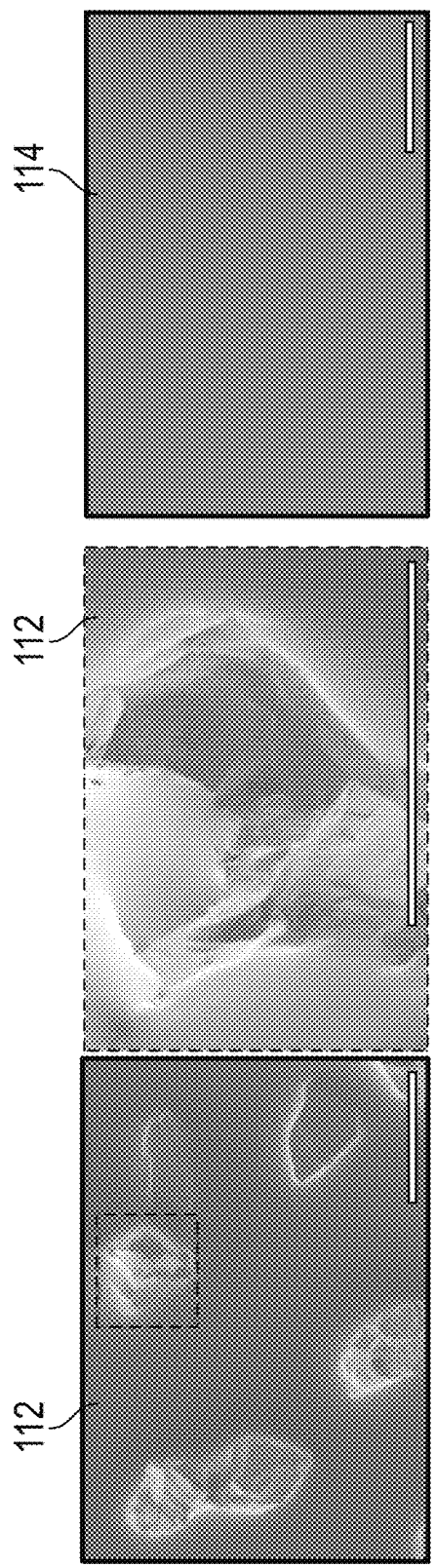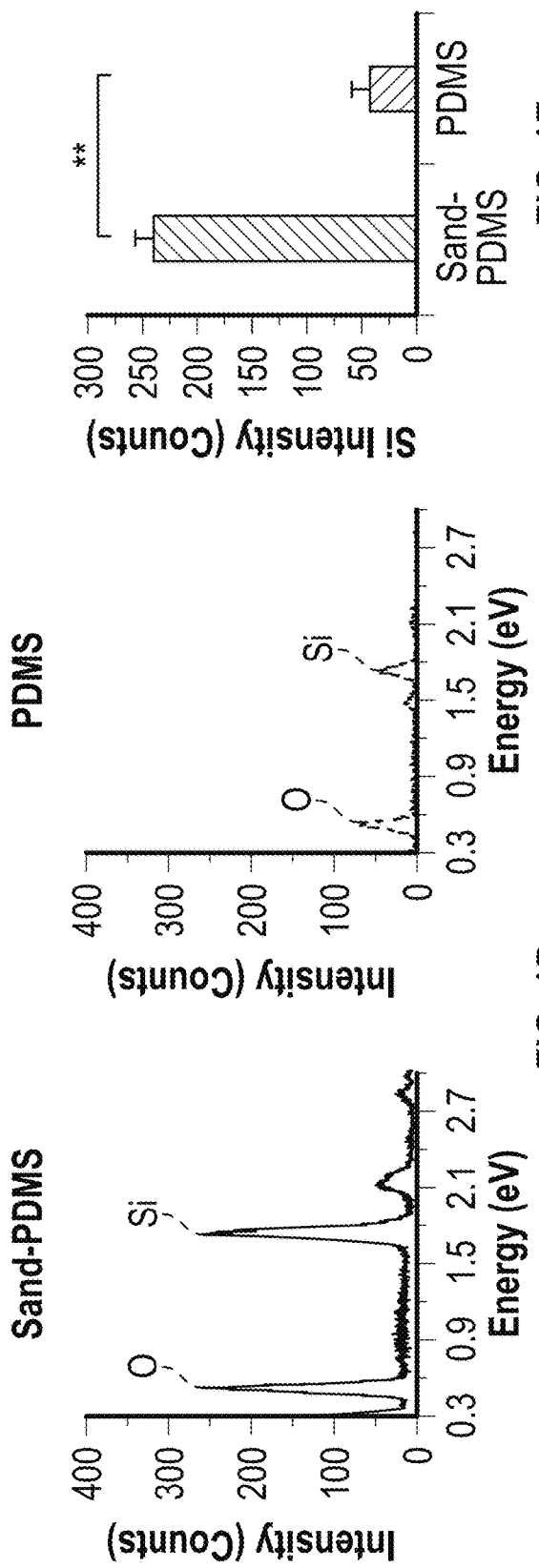
FIG. 1C
FIG. 1D
FIG. 1E

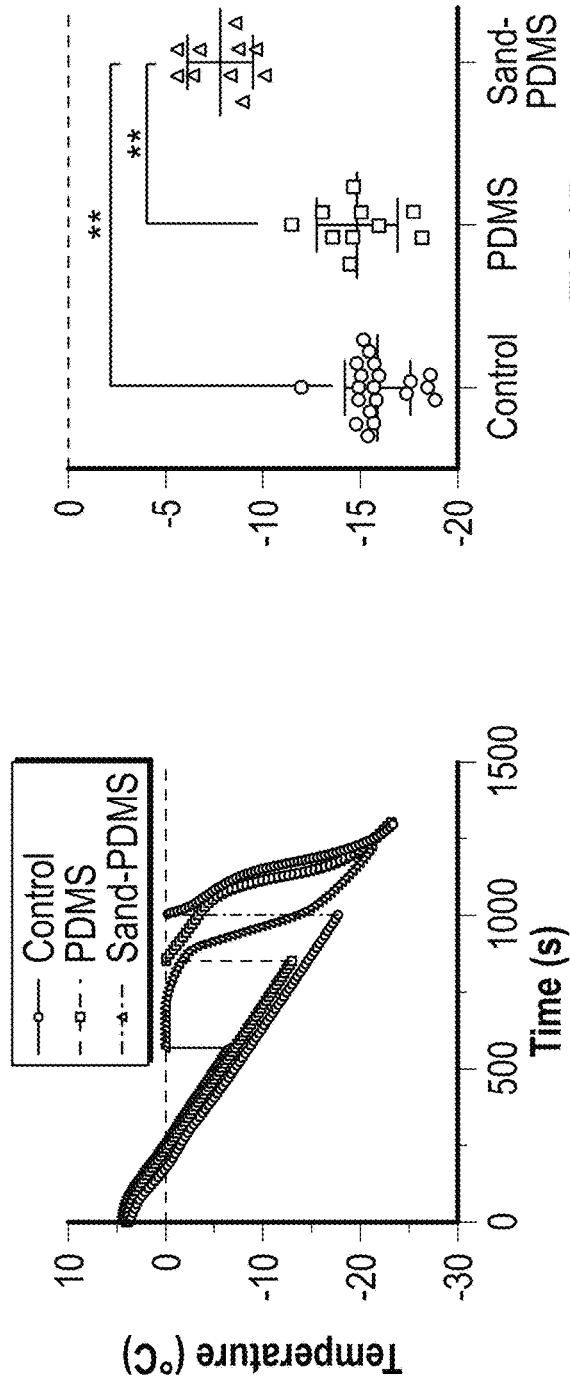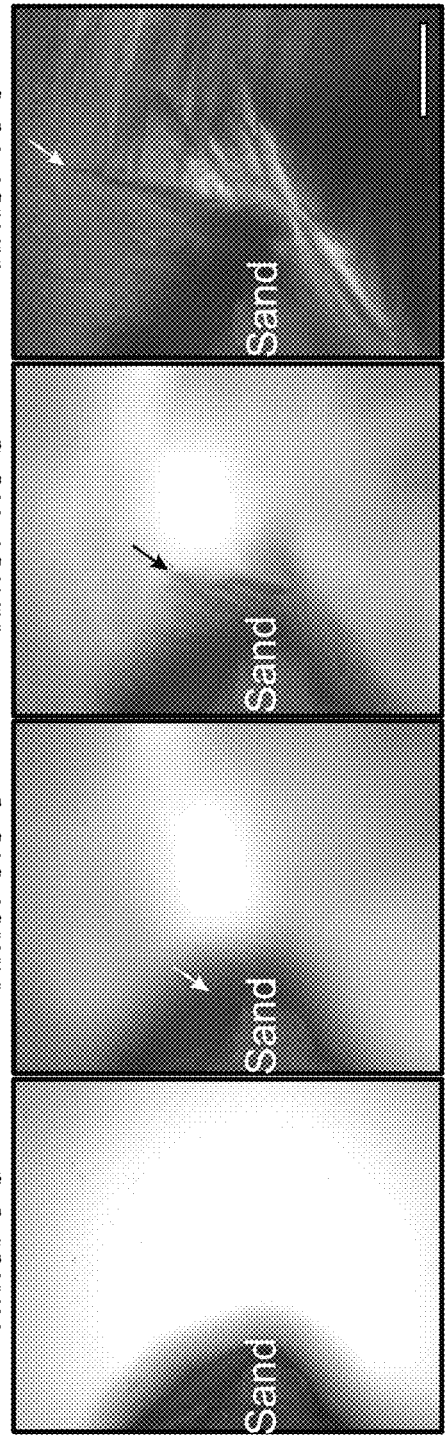
FIG. 2A
FIG. 2B
FIG. 2C

Fresh iPSC-Derived Neural Cells    Fresh iPSC-Derived Cardiomyocytes

Nuclei      TUJ-1      Merge

Nuclei      cTnT      Merge

Ectoderm (Neural Epithelium)    Mesoderm (Cartilage)    Endoderm (Gut Epithelium)

SYSTEM, DEVICE, AND METHOD FOR CELL CRYOPRESERVATION VIA SAND-MEDIATED ICE SEEDING

CROSS REFERENCE TO RELATED APPLICATION(S)

This application claims priority under 35 U.S.C. § 119 to provisional patent application U.S. Ser. No. 63/176,212, filed Apr. 16, 2021. The provisional patent application hereby is incorporated herein by reference in its entirety, including without limitation, the specification, claims, and abstract, as well as any figures, tables, appendices, or drawings thereof.

STATEMENT REGARDING FEDERALLY SPONSORED RESEARCH OR DEVELOPMENT

This invention was made with government support under R01EB023632 awarded by the National Institutes of Health and under CBET1831019 awarded by the National Science Foundation. The government has certain rights in the invention.

FIELD

The presently disclosed subject matter relates generally to a system, device, and method for cell cryopreservation and silicone oxide-based/mediated ice seeding. More particularly, but not exclusively, the silicon oxide-based/mediated ice seeding involves applying a film formed from curing a combination of a PDMS prepolymer, curing agent, and embedded sands to a surface of a device such as a cryovial during a cryopreservation process for preserving cells.

BACKGROUND

The background description provided herein gives context for the present disclosure. Work of the presently named inventors, as well as aspects of the description that may not otherwise qualify as prior art at the time of filing, are neither expressly nor impliedly admitted as prior art.

Human induced pluripotent stem cells (hiPSCs), with their capacity of differentiating into all the three germ layers, have tremendous value for both research to understand human diseases and clinical application to treat the diseases. For example, they have been explored for tissue engineering, disease modeling, and personalized medicine, which requires the ready availability of a large number (e.g., billions) of cells. Therefore, effective long-term cryopreservation or banking of hiPSCs to maintain high viability, function, and pluripotency of the cells for their wide distribution and future use is necessary for the eventual success of the emerging stem cell-based medicine.

Current cryopreservation of hiPSCs utilizes two methods: vitrification and slow-freezing. Although there is a higher survival for hiPSCs using vitrification than slow-freezing, vitrification requires high cooling rates achieved by specialized protocols/devices and/or high concentration of toxic CPA, making it difficult to scale-up for high-volume cell banking. Slow-freezing is convenient and widely used for cryopreservation of hiPSCs, with survival/recovery rates of ~50%. Cryopreservation of hiPSCs is notably more difficult than cryopreservation of human adult stem cells (e.g., tissue-derived stem cells). Adult stem cells can be cryopreserved as single cells by traditional slow-freezing protocols with post-thaw viability up to ~90%. However, hiPSCs are more sensitive to stresses during cell cryopreservation because hiPSCs grow in colonies. And because hiPSCs grow with cell-cell and cell-matrix interactions, hiPSCs may undergo anoikis-induced apoptosis when dissociated into single cells. Therefore, hiPSCs are usually cryopreserved as small clumps supplemented with ROCK inhibitor (RI) and serum to enhance their survival.

Conventional hiPSC cryopreservation uses a slow-freezing method in the presence of 10% dimethyl sulfoxide (DMSO) as the cryoprotectant (CPA) and 10% fetal bovine serum (FBS) or serum replacement. DMSO is effective at protecting the cells from injury during cryopreservation but is highly toxic to cells and tissues at body temperature. Furthermore, DMSO has been found to induce differentiation in more than twenty five (25) human stem cell lines and causes changes in the cellular processes and epigenetic landscape of cardiac cells. The use of fetal bovine serum (FBS) for cryopreservation poses the risk of spontaneous differentiation and introduction of possible xenogeneic pathogens into the hiPSC sample, which may cause adverse effect to patients transplanted with the hiPSCs or their derivatives.

Moreover, culturing hiPSCs at temperatures as high as thirty-seven degrees Celsius (37° C.) is costly and their pluripotency and differentiation capability may decrease gradually over time during culture. Therefore, the quality of hiPSCs may be greatly compromised over long-term culture at these high temperatures.

Various methods have been explored to improve cryopreservation outcome including microencapsulation of cells in alginate hydrogel, nano-warming with magnetic nanoparticles, supplement of nontoxic cryoprotective agents (CPAs) like sugars into a cryopreservation medium, and intracellular delivery of the sugar using cold-responsive nanoparticles.

While efficient and convenient cryopreservation of hiPSCs to bank them in a state of "suspended animation" for their use at a desired future time has been enabled for hiPSC-based personalized medicine, the use of high concentrations of DMSO and serum in contemporary hiPSC cryopreservation protocols poses risks for the clinical use of the cryopreserved hiPSCs.

Thus, there still exists a need in the art for better methods, devices, systems, and protocols regarding the cryopreservation of cells, such as hiPSCs.

SUMMARY

During slow-freezing of cells in aqueous samples, ice nucleates and grows in the extracellular space first. However, uncontrolled spontaneous ice nucleation is a stochastic event that often occurs at temperatures below −10° C., which may be detrimental and often lethal to cells. This is because the lower the subzero temperature when ice nucleation occurs, the more ice embryos can be nucleated (and the finer ice crystals can be formed, due to the same amount of water available for ice embryos to grow in a given space).

At a low subzero temperature like −10° C. or below, the fine ice crystals formed outside cells may easily pierce through the cell membrane to cause physical damage and induce the formation of fine ice crystals of intracellular water that is also deeply supercooled with high tendency of forming ice. Intracellular ice formation ("IIF") has been well-recognized to be a lethal event to cells in general. In addition, the sudden/rapid ice formation at low subzero temperatures can cause a rapid increase in the local osmolality of the extracellular solution around the growing ice crystals, which may induce osmotic shock-associated damage to cells.

In contrast, controlled ice nucleation at a high subzero temperature enables the nucleation of reduced number of ice embryos that gradually grow into large ice crystals outside cells with further cooling, which may allow enough time for intracellular water to gradually diffuse out of cells in response to the gradual freezing of extracellular water to minimize both IIF and osmotic shock. This is crucial for cryopreserving stress-sensitive cells like embryos although the degree of its impact on the outcome of cryopreservation may be cell-type dependent.

A number of methods have been used to control ice nucleation in samples during cryopreservation to improve the outcome. Early studies manually "seed" ice by introducing ice crystals into an undercooled sample. Later, to reduce the risk for sample contamination, precooled probes, metal rods, or forceps have been used to create cold spots from the outside wall of the cell container (e.g., a cryovial), thereby providing localized deep supercooling (usually below $-20°$ C.) to induce ice nucleation in a sample that is above $-10°$ C. overall.

However, manual ice seeding is difficult to standardize and lengthy because it often requires multiple trials to induce ice formation. To address these issues, ice nucleators including the bacterium Pseudomonas syringae, crystalline cholesterol, and silver iodide have been added to the samples for inducing ice formation or seeding ice above $-10°$ C. However, these ice nucleators can be difficult to make in compliance with the current good manufacturing practice (cGMP) and/or are not biocompatible, and therefore are not suitable for cryopreserving clinical grade stem cells.

Inspired by the phenomenon in nature that ice is usually observed next to the bank of rivers, lakes, and ponds at high subzero temperatures in the winter, we discovered that sand particles immobilized in a plastic surface can initiate ice nucleation consistently above $-10°$ C. in this study. Based on this discovery, we further developed a simple and cost-effective method by utilizing sand to seed ice for cryopreservation. This enables serum-free cryopreservation of hiPSCs with high viability (70%) or even very high viability (90%), pluripotency, and function at a much-reduced cryoprotectant concentration (5%). The cryopreserved hiPSCs can attach well and maintain high pluripotency and differentiation capacity in vitro and in vivo. Sand particles can be easily immobilized on the inner plastic surface of the cryovials for holding cells to prevent them from entering the cell sample, and they can be conveniently separated from cells because sand has much higher density than cells. These together with the non-toxic nature of sand may make the sand-mediated ice seeding method very attractive for enhanced cryopreservation of hiPSCs and possibly many other types of cells for widespread research and clinical applications.

The following objects, features, advantages, aspects, and/or embodiments, are not exhaustive and do not limit the overall disclosure. No single embodiment needs to provide each and every object, feature, or advantage. Any of the objects, features, advantages, aspects, and/or embodiments disclosed herein can be integrated with one another, either in full or in part.

It is a primary object, feature, and/or advantage of the present disclosure to improve on or overcome the deficiencies in the art.

It is a further object, feature, and/or advantage of the present disclosure to use controlled ice nucleation catalyzed by sands to greatly improve cell survival rate. For example, hiPSC survival post cryopreservation can be improved from 52.6±3.5% (5% DMSO, no ice seeding) to 90.3±2.5% (5% DMSO, with ice seeding). This increase in survival is similar to other studies regarding the impact of controlled ice nucleation on cell survival using a slow-freezing protocol. Other types of cells susceptible to freezing-induced stresses show a 15-40% increase in survival post-cryopreservation with ice nucleation versus without survival post cryopreservation.

It is still yet a further object, feature, and/or advantage of the present disclosure to employ low DMSO concentration and a short incubation time, as this should be safe for cells. For example, there is a high viability of cells cryopreserved using 5% DMSO with sand-mediated ice seeding.

It is still yet a further object, feature, and/or advantage of the present disclosure to further understand the role that the characteristics of sand played in inducing ice nucleation, specifically surface roughness/sharpness and surface composition (silicon dioxide) that determines the surface properties including hydrophobicity.

The cells disclosed herein can be used in a wide variety of applications. For example, the sand mediated ice-seeding method has the potential to be widely used for cryopreservation of hiPSCs and potentially many other types of human cells. The sand mediated ice-seeding can also facilitate the widespread application of the burgeoning cell-based medicine and for cryopreservation of iPSCs of endangered species to promote animal species conservation.

It is preferred that the sand-mediated cell cryopreservation method be safe to practice, cost effective, and scalable. For example, the cryovials described herein can be adapted to resist excessive heat transfer (the addition and/or subtraction of heat), static buildup, corrosion, and/or mechanical failures (e.g. cracking, crumbling, shearing, creeping) due to excessive impacts and/or prolonged exposure to tensile and/or compressive acting on the apparatus.

The improved cryovial described herein can be incorporated into systems or kits which accomplish some or all of the previously stated objectives.

According to some aspects of the present disclosure, a method comprises using sand to seed ice at a temperature above approximately $-10°$ C. Cryopreservation of the cells occurs with no serum, minimized cryoprotectant, and high cell survival. By way of example, the cells can be selected from the group consisting of stem cells, T cells, and human induced pluripotent stem cells (hiPSCs). However, the method is also suitable for cryopreservation of other types of cells. In an example embodiment, the hiPSC cells cryopreserved so as to retain high pluripotency and functions judged by the pluripotency marker expression, cell cycle analysis, and capability of differentiation into the three germ layers. The sand-mediated cryopreservation method may greatly facilitate the convenient and ready availability of high-quality hiPSCs and other types of cells/tissues for the emerging cell-based translational medicine.

According to some other aspects of the present disclosure, an improved cryopreservation container such as a cryovial comprises a body having at least one opening through which the cells can be moved through, an inner plastic surface that holds the cells to prevent them from entering the cell sample, and a sand-PDMS film applied to the inner plastic surface.

According to some other aspects of the present disclosure, a method of utilizing thawed cells comprises utilizing a sand-mediated ice seeding cell cryopreservation process to cryogenically preserve cells before the cells become the thawed cells, treating the thawed cells with a nuclease that catalyzes the degradation of RNA into smaller components from an enzyme, staining the cells, rinsing the cells, taking measurements with a flow cytometer, and analyzing data based on the measurements. The data can include at least a cell concentration, as well as information pertaining to cell morphology, cell cycle phase, DNA content, and existence or absence of specific proteins on a surface of the cells or in a cytoplasm with the flow cytometer.

According to some additional aspects of the present disclosure, the thawed cells are stained with a fluorescent stain, such as ',6-diamidino-2-phenylindole ("DAPI"). A primary antibody of the at least one antibody is selected from the group consisting of (i) a homeodomain transcription factor, the homeodomain transcription factor optionally comprising octamer-binding transcription factor 4 ("OCT-4"); (ii) a stem cell marker, the stem cell marker optionally comprising stage-specific embryonic antigen 4 ("SSEA-4"); (iii) a neuronal lineage marker, the neuronal lineage marker optionally comprising neuron-specific class III β-tubulin ("TUJ-1"); and (iv) a protein that regulates muscle contraction, the protein optionally comprising cardiac muscle troponin T ("cTnT"); and a secondary antibody of the at least one antibody comprises a polyclonal antibody produced by an inoculation of a non-human mammal, the non-human mammal optionally comprising a mouse, a rabbit, or a goat.

These and/or other objects, features, advantages, aspects, and/or embodiments will become apparent to those skilled in the art after reviewing the following brief and detailed descriptions of the drawings. Furthermore, the present disclosure encompasses aspects and/or embodiments not expressly disclosed but which can be understood from a reading of the present disclosure, including at least: (a) combinations of disclosed aspects and/or embodiments and/or (b) reasonable modifications not shown or described.

BRIEF DESCRIPTION OF THE DRAWINGS

Several embodiments in which the present disclosure can be practiced are illustrated and described in detail, wherein like reference characters represent like components throughout the several views. The drawings are presented for exemplary purposes and may not be to scale unless otherwise indicated.

FIG. 1A shows a schematic illustration of the procedure for preparing the sand-PDMS film, according to some aspects of the present disclosure.

FIG. 1B shows morphology and size distribution of sands before and after sifting them through the mesh strainer, among other things.

FIG. 1C captures a scanning electron microscopy (SEM) image showing the presence and morphology of sands partially embedded in the PDMS film.

FIG. 1D graphs an energy dispersive X-ray spectroscopy (EDXS) quantification of the elemental composition of the sand-PDMS and pure PDMS films. The surface of the sand-PDMS film contains an increased amount of silicon (Si) and oxygen (O) than the pure PDMS surface.

FIG. 1E quantifies Si counts for the sand-PDMS and pure PDMS films using EDXS.

FIG. 2A represents thermal histories in water containing no film (control), pure PDMS film (PDMS), and sand-PDMS film (Sand-PDMS) during cooling.

FIG. 2B quantifies ice-seeding temperature in water under the aforementioned three conditions.

FIG. 2C captures cryomicroscopy images at different times showing ice nucleation and growth around the sand particle during cooling the cell cryopreservation solution at subzero temperatures.

Figure 3A:
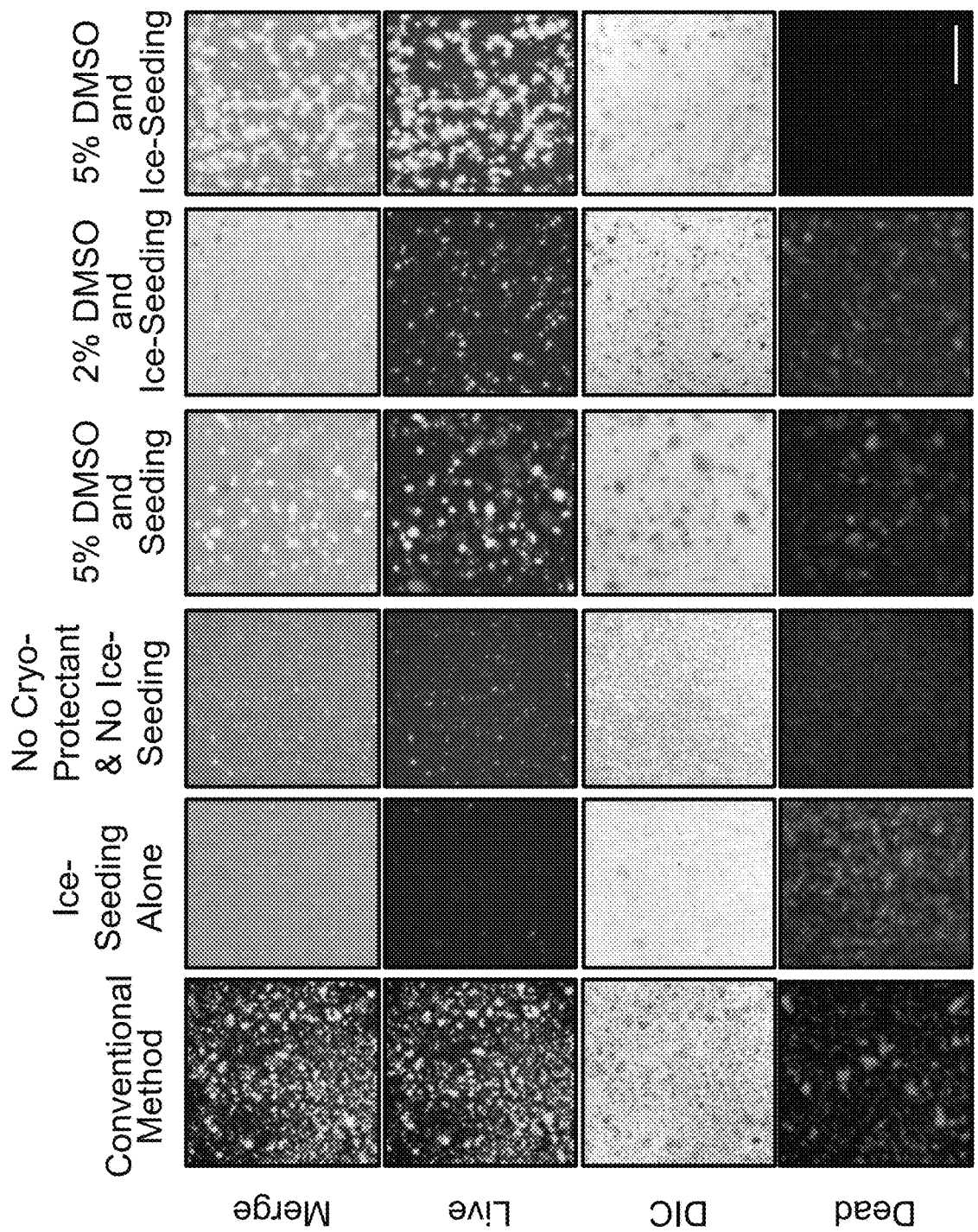
FIG. 3A captures immediate (after two hours incubation at 37° C.) viability of hiPSCs assessed by live/dead staining after cryopreservation with different methods.

An artisan skilled in the art need not view, within isolated figure(s), the near infinite number of distinct permutations of features described in the following detailed description to facilitate an understanding of the present disclosure.

DETAILED DESCRIPTION

The present disclosure is not to be limited to that described herein. Mechanical, electrical, chemical, procedural, and/or other changes can be made without departing from the spirit and scope of the present disclosure. No features shown or described are essential to permit basic operation of the present disclosure unless otherwise indicated.

FIGS. 1A-1E show the preparation and characterization of a sand-PDMS film 106 with embedded sands 100.

Sands 100 can include, but are not limited to including, fine particles of natural occurring materials, such as silicon oxides, quartz, and other naturally occurring minerals known to or that otherwise can seed ice in the atmosphere. For example, silicon dioxide-based sands do not require any material or surface modification to achieve ice nucleation, making them convenient and cost-effective to use.

As shown in FIGS. 1A (and also FIG. 6, discussed infra), the sands 100 can be rinsed overnight with water, autoclaved, dried, and then mechanically sifted onto a thin and uncured PDMS layer over a fully cured PDMS film 102. The PDMS film 102 preferably has a thickness between one hundredth millimeter (0.01 mm) and one hundred millimeters (100 mm), more preferably a thickness between one tenth millimeter (0.1 mm) and ten millimeters (10 mm), and most preferably a thickness between one half millimeter (0.5 mm) and one and one-half millimeters (1.5 mm). The mechanical means through which sifting can occur can include, but is not limited to, use of a mesh strainer.

The PDMS film 102 embedded with sand 100 can then be baked in heating step 104 (e.g., 75° C. for 30 min) to form the sand-PDMS film 106. After baking, the resultant sand-PDMS films 106 are cut into small pieces. Each piece of the sand-PDMS film 106 is soft and can be easily deformed onto the shape of the inner wall 110 of a cryovial 108. The sand-PDMS film 106 includes one smooth surface without any sand 100. The smooth surface is the surface which attaches to the inner wall 110. The sand-PDMS film 106 was cut into small pieces and each piece was stuck/attached onto an inner wall 110 of a cryovial 108 to seed ice, thereby enhancing the outcome of cryopreservation of cells, such as human induced pluripotent stem cells (hiPSCs).

HiPSCs can be derived from the somatic cells like skin fibroblasts and blood cells of a specific person (patient or healthy donor) and have the capability of self-renewal and differentiation into somatic cells of all three germ-layers. This eliminates the ethical concern of using embryonic stem cells.

As shown in FIG. 1B, morphology and size distribution of sands 100 before shifting varies more than after sifting them through a mesh strainer. A high-magnification view of the sifted sands is shown on the left where the sharp morphology of the sands is more appreciable. The size distribution was quantified based on the area of sand particles 100 on the films 102.

As shown in FIG. 1C, the presence and morphology of sands partially embedded in the PDMS film 106 can be captured using scanning electron microscopy (SEM).

As shown in FIG. 1D, intensity of an energy dispersive X-ray spectroscopy (EDXS) of the elemental composition of both sand-PDMS films 106 and pure PDMS films can be graphed as a function of energy (eV). The surface of the sand-PDMS film 112 contains an increased amount of silicon (Si) and oxygen (O) when compared to the pure PDMS surface 114. Natural sand is made of silicon dioxide ($SiO_2$). Exposed sand can nucleate/seed ice in the cryopreservation solution outside cells during cooling, similarly to that observed near river/lake/pond bank in nature.

As shown in FIG. 1E, Si counts for the sand-PDMS 106 and pure PDMS films can be quantified using EDXS. In FIG. 1E, $p<0.01$ (n=3 independent runs) and the scale bars indicate 200 μm.

FIGS. 2A-2C capture sand enabling ice seeding at a high subzero temperature.

Representative thermal histories in water containing no film (control), pure PDMS film (PDMS), and sand-PDMS film (sand-PDMS) during cooling can be seen in FIG. 2A. Ice-seeding in the sample can be detected by a sudden temperature rise due to the release of latent heat of fusion as a result of ice nucleation and growth. A sudden increase in temperature indicates ice seeding (which releases latent heat) in the sample.

As shown in FIG. 2B, quantitative data of the ice-seeding temperature in water under the aforementioned three conditions can be measured. For the ** shown in FIG. 2B, $p<0.01$ (n=10 (for sand-PDMS film and pure PDMS film) or 20 (for Control), independent runs).

As shown in FIG. 2C, different times showing ice nucleation and growth around the sand particle during cooling the cell cryopreservation solution at subzero temperatures were captured with cryomicroscopy images, wherein the scale bar equals 100 μm. Sands 100 are capable of seeding ice at the high subzero temperature and cooling the cryopreservation solution in a controlled manner. The controlled manner could be, by way of a non-limiting example, a decrease of one degree Celsius per minute.

Figure 3B:
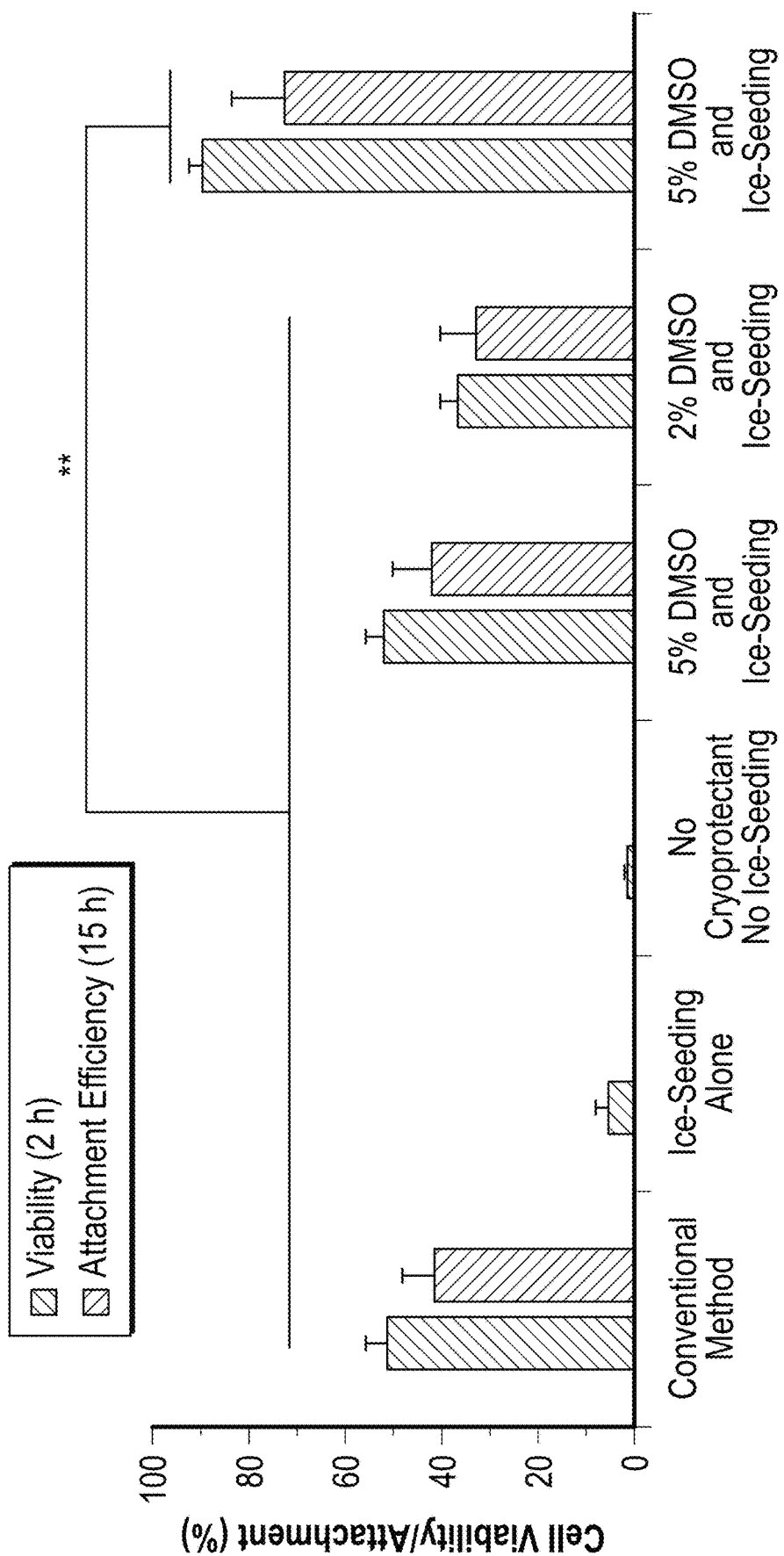
FIG. 3B graphs quantitative data of the hiPSC immediate viability and attachment efficiency after various cryopreservation conditions.

FIGS. 3A-3B shows immediate and long-term viability of hiPSCs after cryopreservation under various conditions.

As shown in FIG. 3A, the immediate (e.g., after 2 h incubation at 37° C.) viability of hiPSCs assessed by live/dead (e.g., green/red) staining after cryopreservation with different methods, including: a conventional method (10% DMSO+10% serum with no ice seeding), sand-mediated ice-seeding alone, no cryoprotectant and no ice-seeding, 5% DMSO with no ice seeding, 2% DMSO with ice-seeding, and 5% DMSO with ice seeding. The scale bar included in the figure represents 500 μm.

In other words, the solution described herein seeds/nucleates ice at high subzero temperature during cooling hiPSCs for cryopreservation with a good outcome and reproducibility. This allows serum-free cryopreservation of hiPSCs with high viability and quality at a much reduced (half) DMSO concentration.

As shown in FIG. 3B, quantitative data of the hiPSC proves both immediate viability and long-term viability (attachment efficiency) after the various cryopreservation conditions of FIG. 3A. For quantifying the attachment efficiency, the cryopreserved cells were thawed and cultured for fifteen (15) hours, and the number of attached cells was counted by hemacytometer. The attachment efficiency is calculated as the percentage of cells counted after cryopreservation out of the number of cells initially cryopreserved. For the ** shown in the FIG. 3B, $p<0.01$ (n=3 independent runs) for the comparison of both immediate viability and attachment efficiency.

It can be beneficial not to remove DMSO from the sample immediately after thawing the sample. Not immediately removing DMSO can avoid centrifuging and rinsing the hiPSCs that just suffer the stresses during thawing. It can also lessen susceptibility to stresses associated with centrifugation and washing.

FIGS. 4A-4E show cryopreservation with sand-mediated ice seeding and that 5% DMSO can maintain the hiPSC pluripotency and cell cycle.

Figure 4A:
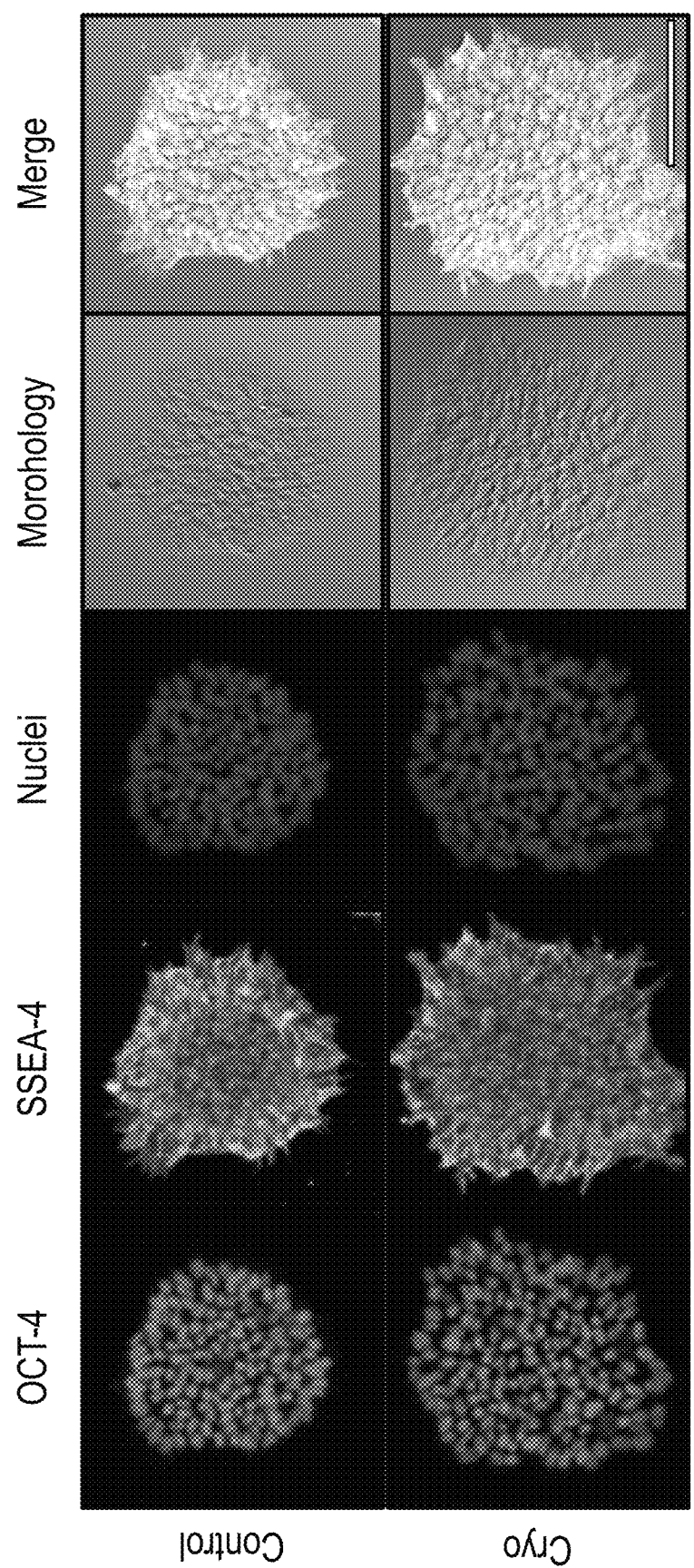
FIG. 4A captures images of cryopreserved (Cryo) hiPSCs showing typical colony morphology and high expression of pluripotency protein markers OCT-4 and SSEA-4, similar to fresh (control) hiPSCs with no cryopreservation.

As shown in FIG. 4A, cryopreserved (Cryo) hiPSCs show typical colony morphology and high expression of pluripotency protein markers OCT-4 and SSEA-4, similar to fresh (control) hiPSCs with no cryopreservation. The scale bar of FIG. 4A represents 100 μm.

Figure 4B:
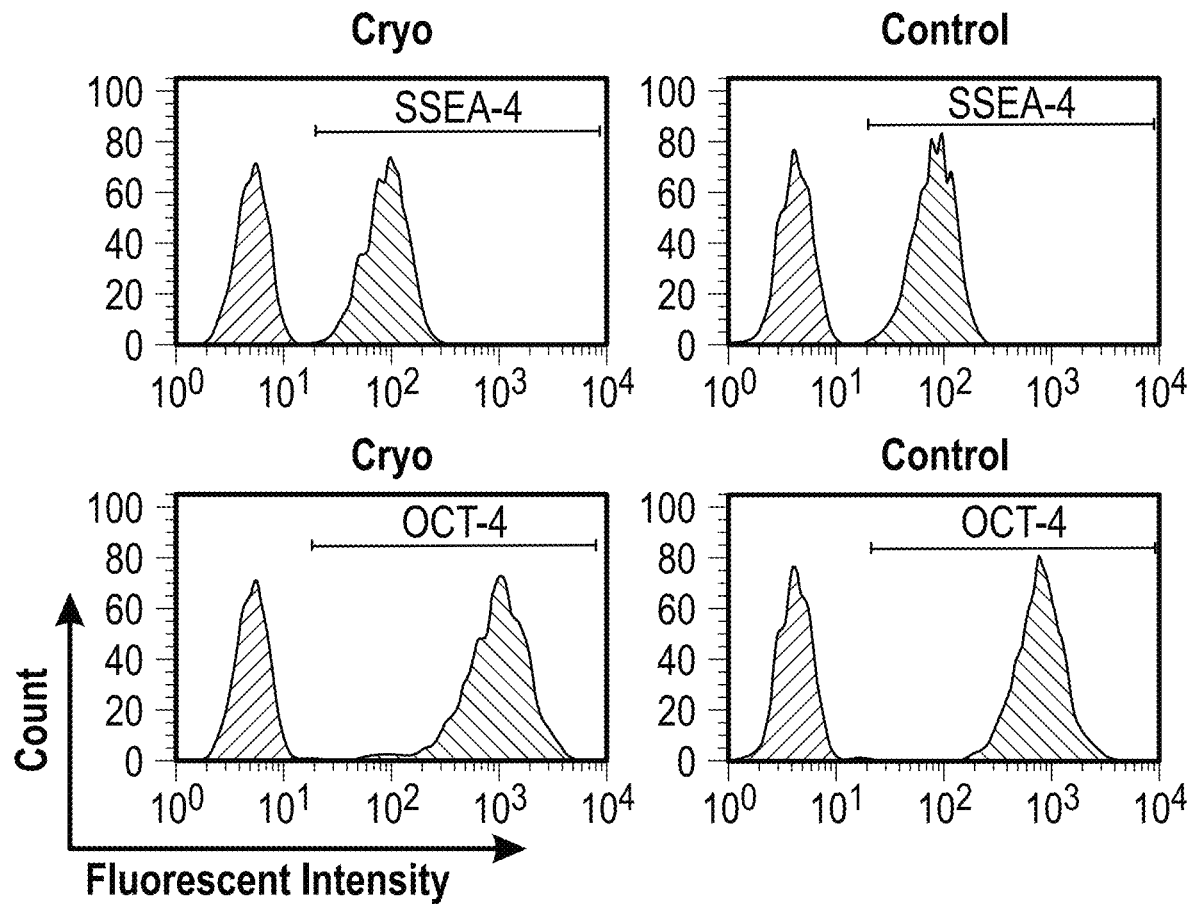
FIG. 4B shows representative peaks on a graph of count as a function of fluorescent intensity for pluripotency protein markers SSEA-4 and OCT4.
Figure 4C:
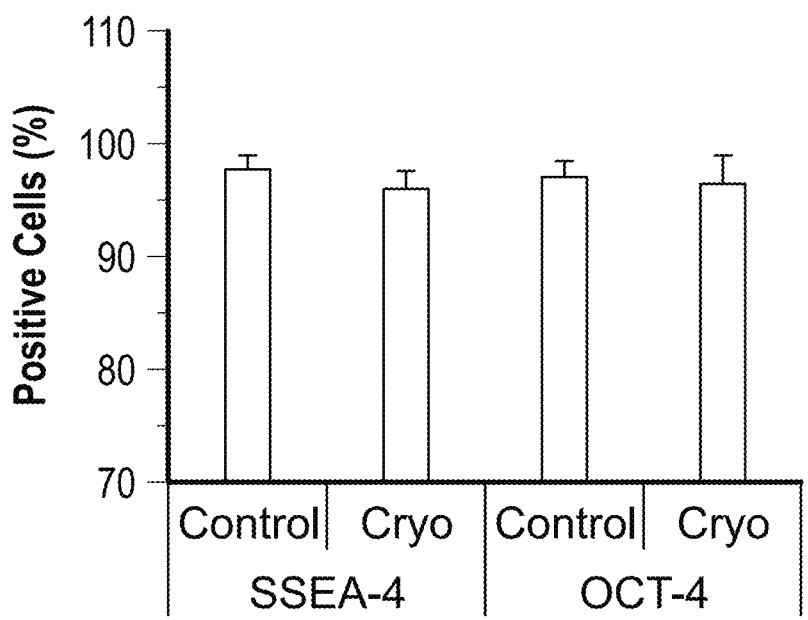
FIG. 4C shows quantitative data wherein positive cell % is charted for pluripotency protein markers SSEA-4 and OCT4, including both control and cryo-data therefore.

As shown in FIGS. 4B-4C, representative peaks and quantitative data (FIG. 4C: n=3 independent runs) form flow cytometry analyses, showing the cryopreserved hiPSCs highly express pluripotency protein markers SSEA-4 and OCT4 similar to the fresh control hiPSCs with no statistically significant difference. The peaks on the left side of FIG. 4B are isotype controls.

Figure 4D:
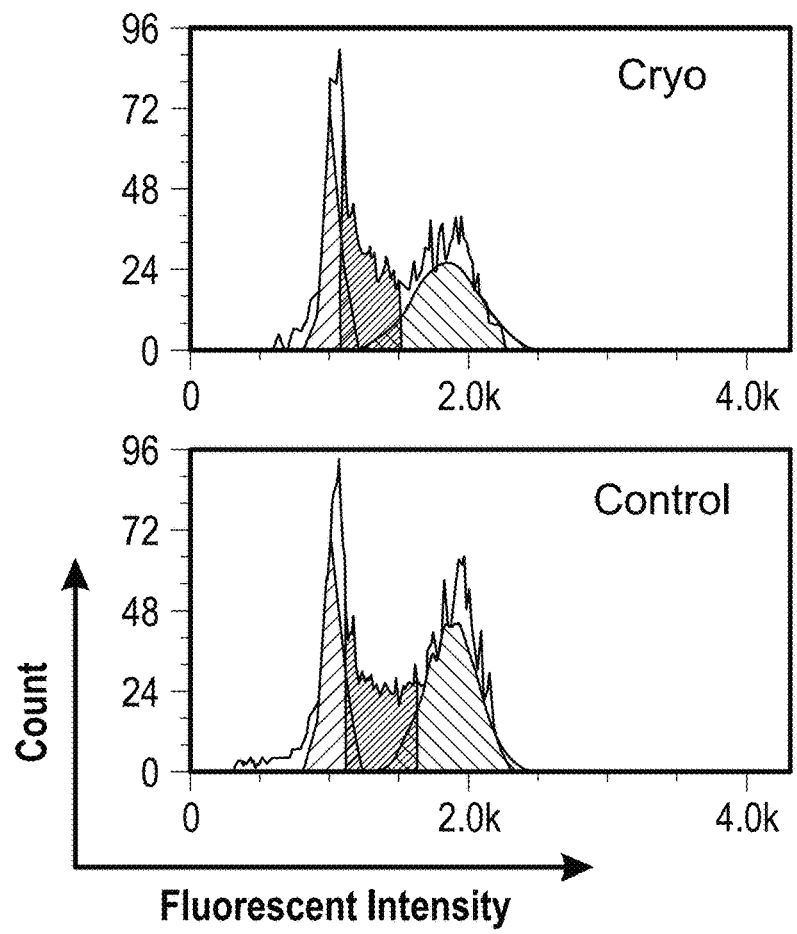
FIG. 4D shows representative peaks on a graph of count as a function of fluorescent intensity in the G1, S, and G2/M phases of the cell cycle.
Figure 4E:
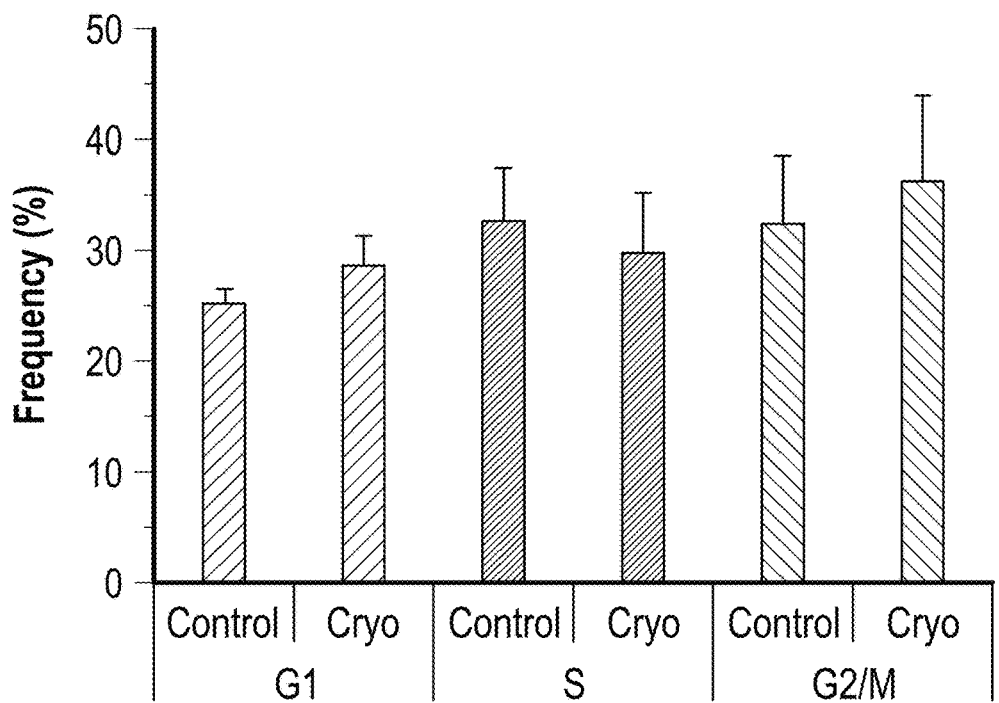
FIG. 4E shows quantitative data wherein positive frequency % is charted for the in the G1, S, and G2/M phases of the cell cycle, including both control and cryo-data therefore.

As shown in FIGS. 4D-4E, representative peaks and quantitative data (FIG. 4E: n=3 independent runs) form flow cytometry analyses, showing no statistically significant difference in the cell cycle distribution between the cryopreserved and fresh control hiPSCs.

Figure 5B:
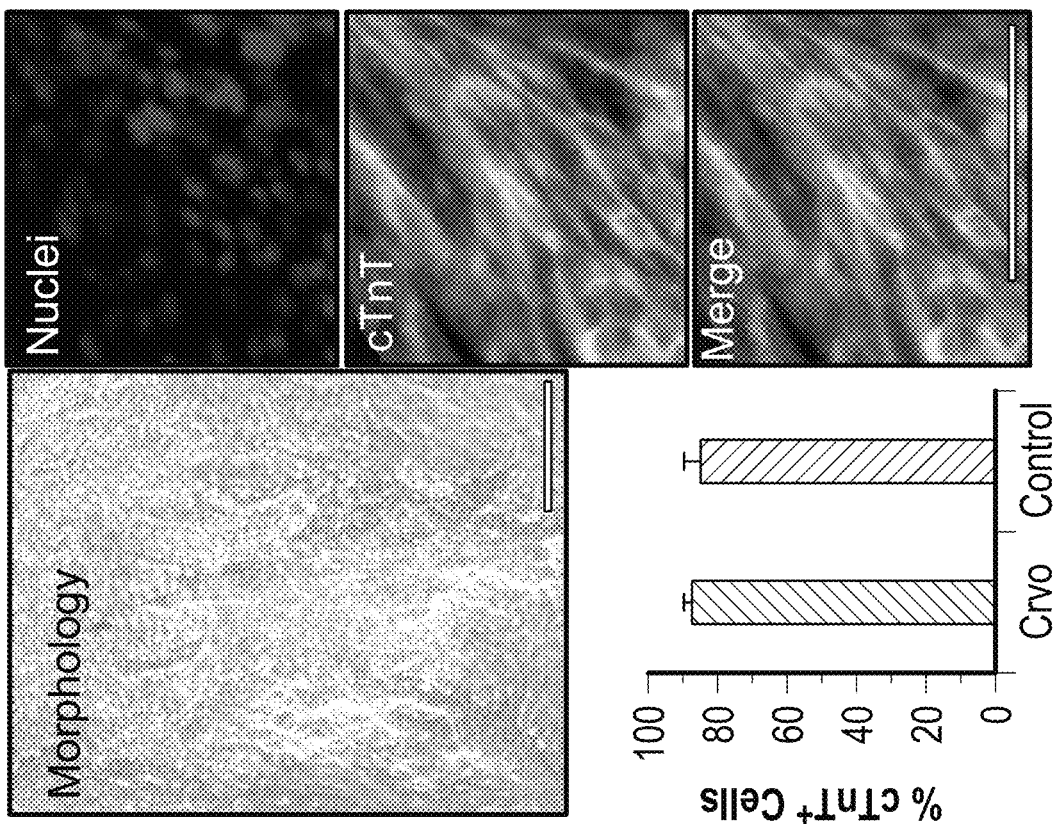
FIG. 5B shows the cryopreserved hiPSCs can efficiently differentiate into cells that highly express the cardiac specific markers cTnT. Images are captured wherein cell nuclei are made visible by DAPI staining. Related data accompanies the images and is quantified in the bar graph in the lower left-hand portion of the figure.
Figure 5A:
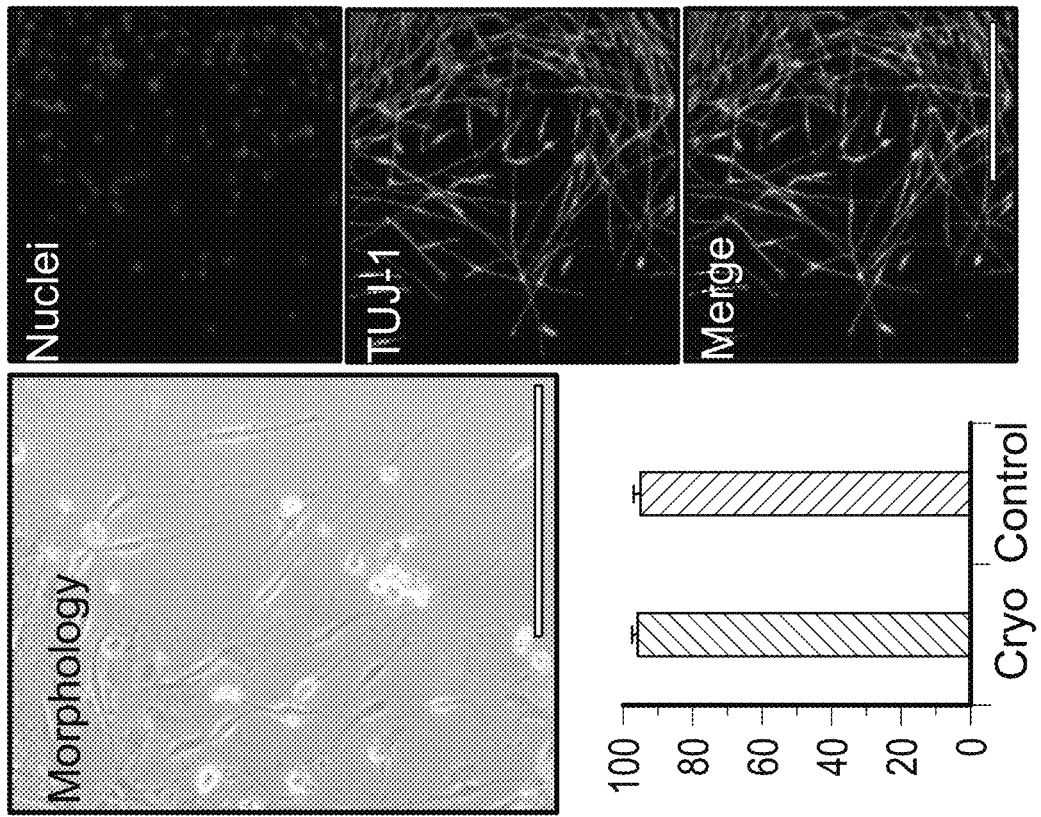
FIG. 5A shows the cryopreserved hiPSCs can efficiently differentiate into cells with typical neural cell morphology (neurites extending out of the cell body) and high expression of the neural specific marker TUJ-1. Images are captured wherein cell nuclei are made visible by 4',6-diamidino-2-phenylindole ("DAPI") staining. Related data accompanies the images and is quantified in the bar graph in the lower left-hand portion of the figure.
Figure 5C:
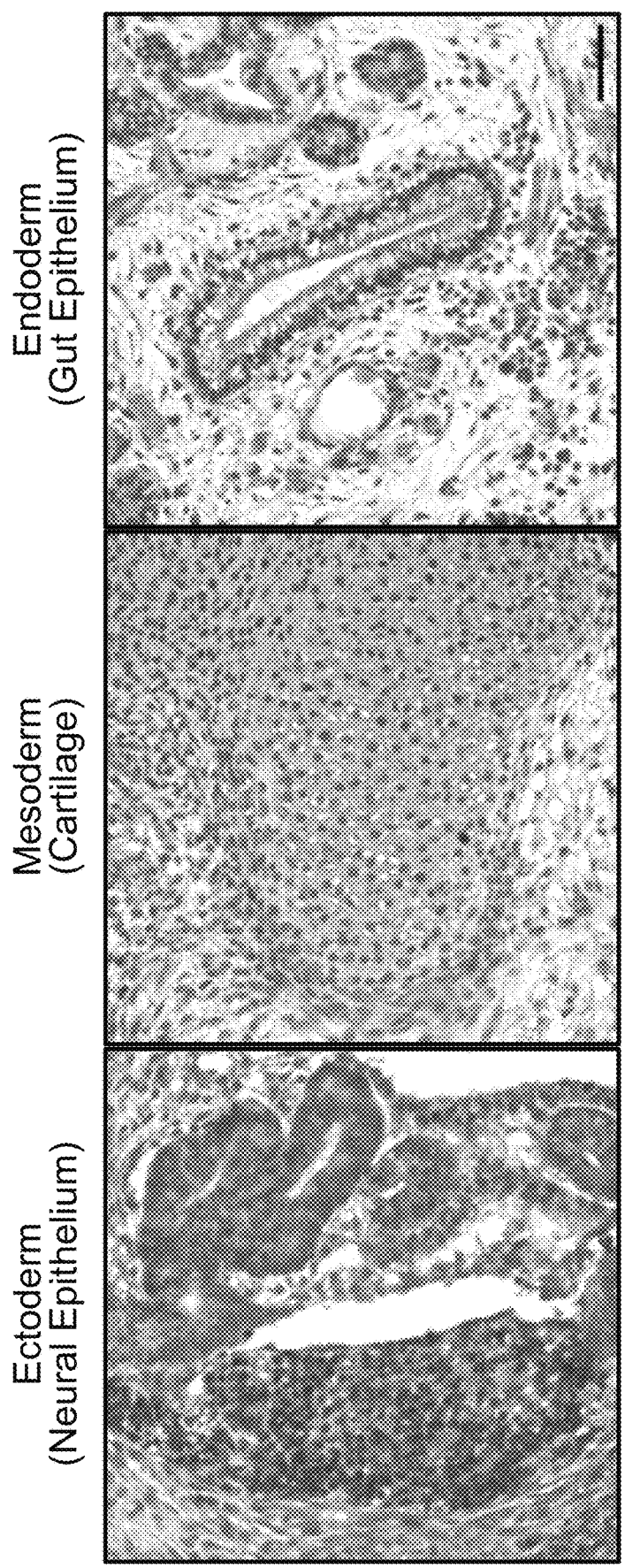
FIG. 5C shows teratomas grown from the cryopreserved hiPSCs contain tissues from all the three germ layers including the ectoderm (neural epithelium with hypernucleated neuroectodermal structures), mesoderm (the nidus of cartilage with surrounding condensed mesenchymal cells), and endoderm (gut epithelium with subnuclear vacuoles and tube-like structure).

The images of FIGS. 5A-5C evidence cryopreservation with sand-mediated ice seeding and 5% DMSO maintain the differentiation capacity of the hiPSCs. The scale bars shown throughout FIGS. 5A-5C indicate 100 μm.

Figure 6:
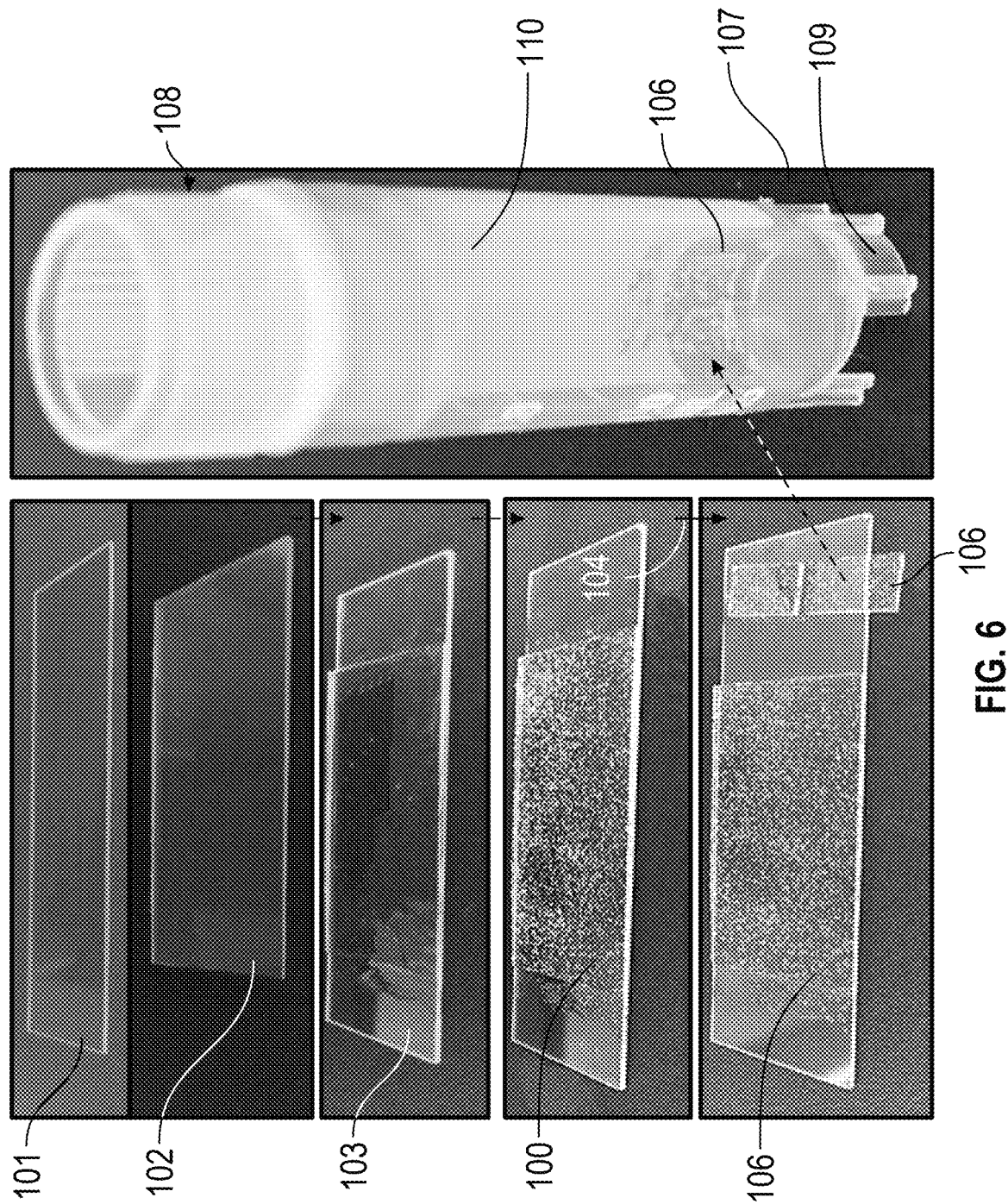
FIG. 6 shows a method of preparing a sand-PDMS film loaded cryovial.

As shown in FIG. 6, a mixture of a PDMS prepolymer and a curing agent is spread onto a plain microscope glass slide to form a thin PDMS film of ~1 mm thick. Uncured PDMS is thinly spread onto the cured PDMS film to act as an adhesive for the sands. Then, sands are sifted onto the uncured PDMS through a mesh strainer with 200 μm openings. Afterward, the PDMS film with sands is cured at 75° C. for 30 mins to form the sand-PDMS film that is further trimmed and cut into 3 mm×5 mm pieces for sticking/attaching on the inner wall of cryovials via the smooth side of the sand-PDMS film.

The cryovial 108 can include a base 109 such that the cryovial 108 can stand upright with respect to a flat surface(s) 107, such as a surface that of a table, counter, working area, etc. By way of a non-limiting example, the base 109 can include legs, a planar platform, and/or any other suitable support structure for immobilizing the cryovial 108 with respect to the surface 107.

Figure 7:
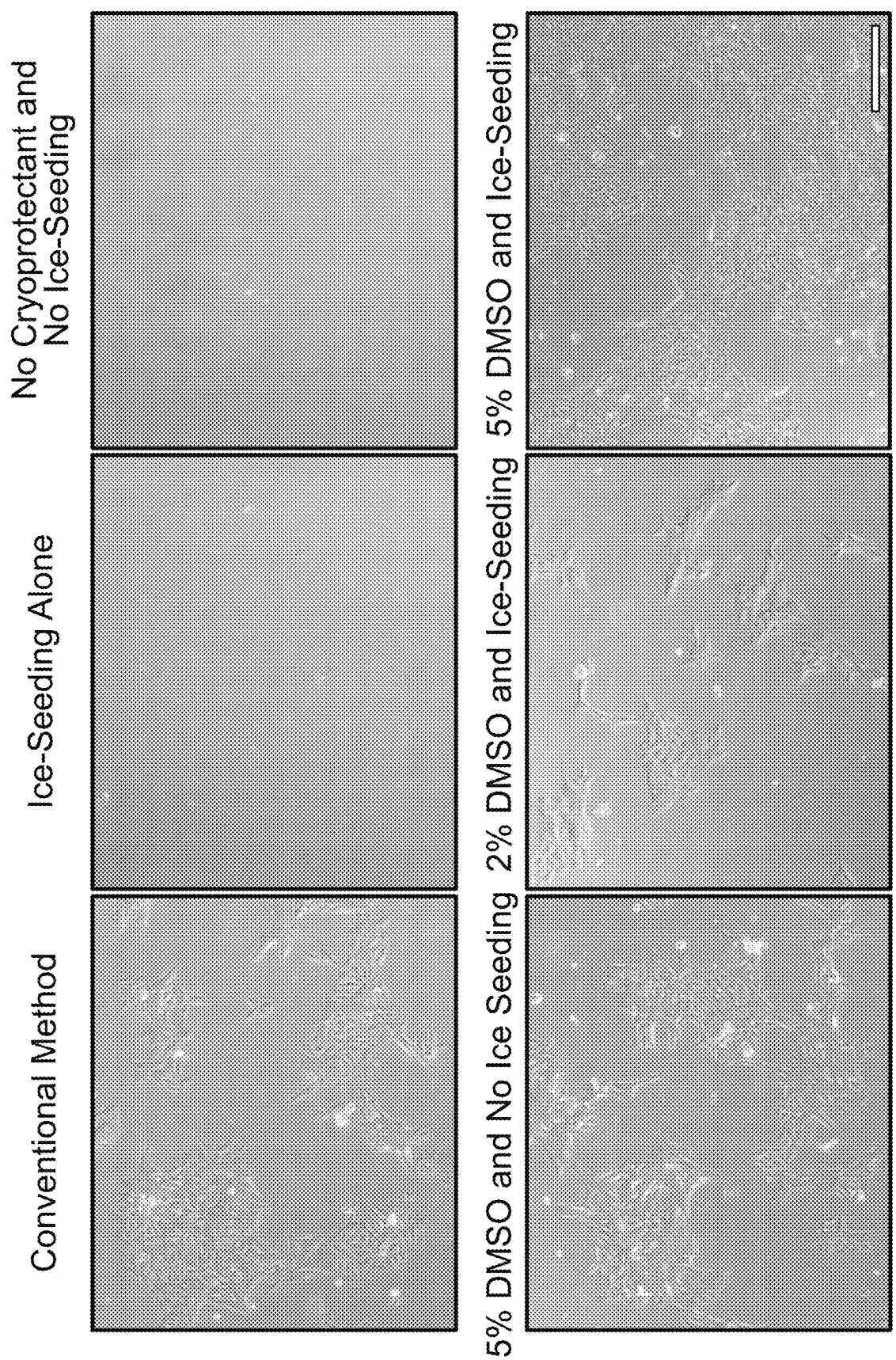
FIG. 7 shows morphology of hiPSCs cryopreserved under different conditions after thawing and fifteen hours (15 h) of culturing.

As shown in FIG. 7, morphology of hiPSCs can be cryopreserved under different conditions after thawing and culturing. The group of cryopreservation with sand-mediated ice seeding and 5% DMSO has the most attached cells. The scale bar of FIG. 7 indicates 100 μm.

FIGS. 8A-8D evidence the differentiation capacity of freshly controlled hiPSCs. The scale bars shown throughout FIGS. 8A-8D indicate 100 μm.

Figure 9A:
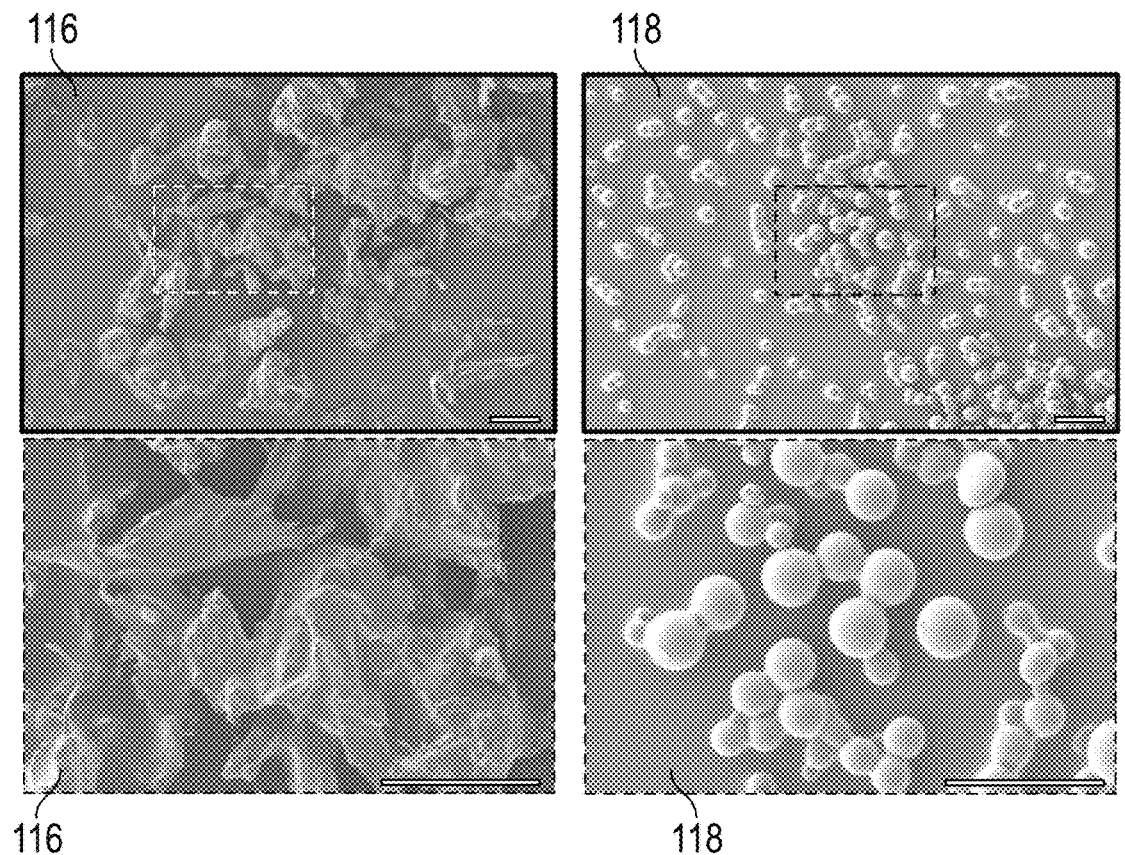
FIG. 9A captures a scanning electron microscopy (SEM) image that shows the presence and morphology of plastic shards and glass beads partially embedded in the PDMS film.
Figure 9B:
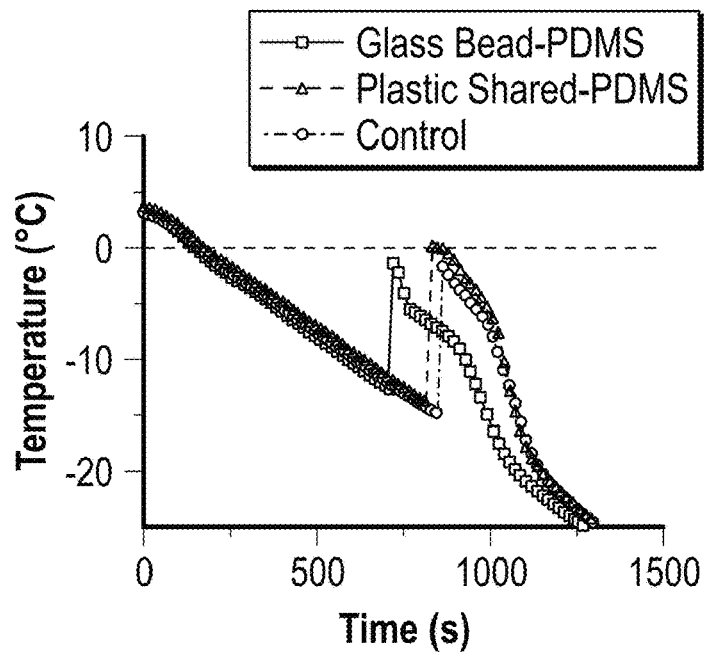
FIG. 9B graphs representative thermal histories in water containing no film (control), plastic shard-PDMS film, and glass bead-PDMS film during cooling, wherein a sudden increase in temperature indicates ice seeding (which releases latent heat) in the sample.
Figure 9C:
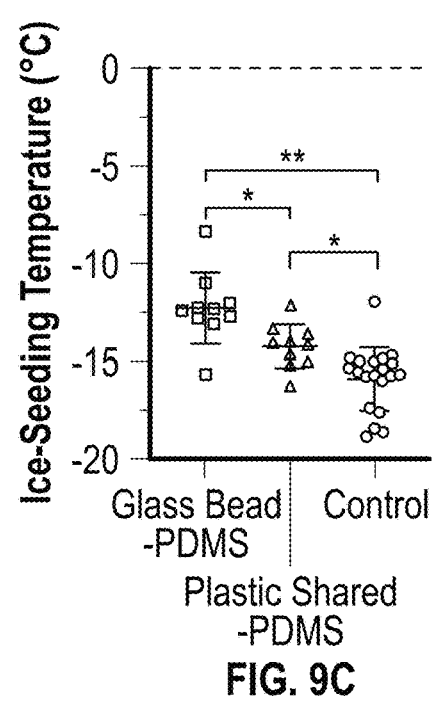
FIG. 9C charts quantitative data of the ice-seeding temperature in water under the conditions of FIG. 9B.

FIGS. 9A-9C compare images of ice nucleation/seeding with respect to glass beads and plastic shards and compare data relating to the same and that of a control. In FIG. 9A, the detailed morphology of the plastic shards and glass beads are more appreciable in the high-magnification views of the dashed line-boxed areas and the scale bars indicate 200 μm. In FIGS. 9B-9C *, $p<0.05$, **, $p<0.01$, wherein n=10 for plastic shard-PDMS film and glass bead-PDMS film and n=20 for the control (independent runs).

The glass beads are made of silicon dioxide (as with sands) with a smooth surface (FIG. 9A), and the differences between the two can be used to better understand the effect of surface roughness/sharpness on ice seeding. The plastic shards have sharp edges as with sands but a different composition from sands, which is examined to understand the effect of composition that determines the surface property including hydrophobicity (sand is more hydrophilic than the plastic shards) on ice seeding.

The glass bead-PDMS film can improve the ice seeding temperature significantly for water without anything for ice seeding, as shown in FIG. 9B. However, it is significantly lower than the ice seeding temperature for the sand-PDMS film 106. This indicates both the silicon dioxide material and surface roughness/sharpness are important for ice seeding.

The ice seeding temperature for the plastic shard-PDMS film of FIGS. 9B-9C is also significantly higher than that for control (i.e., water without anything for ice seeding) and significantly lower than that for the sand-PDMS film 106. In addition, the ice seeding temperature for plastic shard-PDMS film is not significantly different from that of pure PDMS film 102 while the ice seeding temperature for glass bead-PDMS film is significantly higher than that of pure PDMS film 102, suggesting that the surface roughness/sharpness may be secondary to the surface composition (although both are important and might work synergistically) in determining the ice seeding temperature.

It is to be appreciated that at least some of the methods already explored in the art to improve cryopreservation outcome may be combined with the sand-mediated ice-seeding methods described herein. This could further have the potential to reduce or even eliminate the DMSO needed for cryopreservation of the hiPSCs with high functional survival. Such methods include, at least, microencapsulation of cells in alginate hydrogel, nano-warming with magnetic nanoparticles, supplement of nontoxic CPAs like sugars into the cryopreservation medium, and intracellular delivery of the sugar using cold-responsive nanoparticles.

Finally, the methods described herein may be applied to cryopreserve the iPSCs of non-human endangered species with high functional survival, which is valuable for animal species conservation.

EXAMPLES

1. Materials and Methods
1.1 Cell Culture

The DF19-9-11T.H and IMR90-1 hiPSC lines were purchased from WiCell (Madison, WI, USA). The cells were cultured in StemFlex medium (ThermoFisher, Gaithersburg, MD, USA) on Matrigel (Corning, NY, USA)-coated plates in thirty-seven degrees Celsius (37° C.) five percent carbon dioxide (5% $CO_2$) incubator. The cells were passaged at a ratio between 1:4 and 1:5 twice a week. Versene (Gibco, Gaithersburg, MD, USA) which contains 0.48 nM ethylenediaminetetraacetic acid (EDTA) in phosphate buffered saline (PBS) was used to detach the cells at thirty-seven degrees Celsius (37° C.) for two minutes (2 min) for passaging or further uses.

1.2 Fabrication of Sand-PDMS Film for Cryopreservation

Sands were purchased from Walmart (Landover Hills, MD, USA) and were rinsed under running tap water overnight in a one hundred milliliter (100 mL) beaker with agitation by a glass stir bar for ten minutes (10 min). The sand was then washed twice with fifty milliliters (50 mL) deionized water. Afterwards, the sands were autoclaved at one-hundred twenty-one degrees Celsius (121° C.) for thirty minutes (30 min) and baked in a seventy-five degrees Celsius (75° C.) oven for six hours (6 h) to dry.

Polydimethylsiloxane (PDMS, Dow SYLGARD 184 Silicone Encapsulant, Dow, Midland, MI, USA) prepolymer was mixed with its curing agent at a weight ratio of 10:0.5 (prepolymer:curing agent). One milliliter (1 mL) of mixture was poured onto a microscope glass slide (dimensions: 75×26×1 mm) and air bubbles were removed under vacuum for twenty minutes (20 min). Afterwards, the PDMS was cured by baking in a seventy-five degrees Celsius (75° C.) oven for two hours (2 h). Fifty microliters (50 µL) of an uncured PDMS mixture were then evenly spread with the aid of a pipette tip on top of the cured PDMS on the glass slide to form a sticky fluid layer.

Afterward, the dry sands were sifted through a mesh strainer (opening size: two hundred micrometers, 200 µm) at approximately five centimeters (~5 cm) above to drop and partially embed the sands in the uncured PDMS sticky fluid layer. The slide with PDMS and sand was further baked in the oven at seventy-five degrees Celsius (75° C.) for thirty minutes (30 min). The cured sand-PDMS film was gently peeled off from the slide with the help of a blade and then cut into pieces of three millimeters (3 mm)×five millimeters (5 mm) (width×length). Finally, each of the sand-PDMS pieces was attached to the inside wall of a cryovial and the sand-PDMS piece containing cryovials were autoclaved at one hundred twenty-one degrees Celsius (121° C.) for thirty minutes (30 min) before their use to hold hiPSC sample for cryopreservation.

For making the plastic shard-PDMS film, plastic shards were scratched off a polystyrene cell culture plate (ThermoFisher) using a single edge razor blade onto the uncured PDMS sticky layer (with all other steps being the same as that making the sand-PDMS film). Glass beads of forty to seventy micrometers (40-70 µm) in size were purchased from Microspheres-Nanospheres (C-PGL-07, Microspheres-Nanospheres, NY, USA). The glass beads were partially embedded in the PDMS film following the same procedure for making sand-PDMS film.

1.3 Fabrication of Sand-PDMS Film for Cryopreservation

For the scanning electron microscopy (SEM) imaging, the sand-PDMS films were cut into small pieces of one square centimeter (1 cm$^2$) and attached on the SEM sample holder. The samples were sputter-coated with gold using a Cressington-108 sputter coater for two minutes (2 min) at fifteen milliamps (15 mA). Afterwards, the samples were imaged with a Hitachi (Tokyo, Japan) SU-70 FEG scanning electron microscope at 5.0 kV. Energy dispersive x-ray spectroscopy (EDXS, Hitachi SU-70 FEG SEM, Tokyo, Japan) was used for elemental analysis of the surface of the plain PDMS and sand-PDMS films. The plain PDMS film was prepared in the same way as that for preparing the sand-PDMS films except that no sand was plated.

For quantifying the size of sand particles before and after sifting, brightfield microscopy images of sand particles partially embedded in the PDMS film before and after sifting through the mesh strainer were analyzed using Image J (version 1.47) to measure the area of sand particles on the film. Images from ten (10) random areas of the film containing a total of sixty-five (65) sand particles were analyzed for both conditions (i.e., before and after sifting through the mesh strainer).

1.4. Measurement of Ice-Seeding Temperature

To measure the ice-seeding temperature, a piece of sand-PDMS film was attached to the inside wall of a two milliliter (2 mL) glass vial, followed by adding five-hundred microliters (500µ) of deionized water. The ice seeding temperatures of water in the same cryovials containing either a PDMS-film without sand or no film at all were studied as controls. A K-type thermocouple (Omega, Norwalk, CT, USA, 0.05 inch in diameter) was then placed in water in the glass vial. The vials were placed onto the shelf of a SP Virtis AdVantage Pro benchtop lyophilizer (SP, Warminster, PA, USA) and cooled to four degrees Celsius (4° C.). Then the sample was cooled to negative twenty-five degrees Celsius (−25° C.) with a twenty-five minute (25 min) ramp time. The thermocouple was connected to a Keysight Technologies (Santa Rosa, CA, USA) 34970A Data Acquisition/Data Logger Switch Unit to record the temperature over time. The temperature at the time when there was a sudden increase in temperature due to the latent heat release associated with ice formation during the cooling process, was recorded as the ice-seeding temperature. Ice-seeding temperatures of the plastic shard- and glass bead-PDMS films were measured in the same way.

1.5. Cryomicroscopy Study of Sand-Mediated Ice Formation

Cryomicroscopy was conducted using a Linkam FDCS196 (Tadworth, UK) freeze-drying stage mounted on a Zeiss (Oberkochen, Germany) A1 Axio Scope, for which a drop (200 µL) of the cryopreservation solution made of the mTeSR medium (STEMCELL Technologies, Vancouver, Canada) supplemented with 5% DMSO, and sands were added in the sample holder at room temperature. The sample holder with the sands immersed in the solution was then loaded into the freeze-drying stage for controlled cooling at one degree Celsius per minute (1° C. min$^{-1}$) to negative twenty degrees Celsius (−20° C.). Real-time images were captured with a FLIR (Wilsonville, OR, USA) Grasshopper three color camera every half-second (0.5 s).

1.6. Cell Cryopreservation

The cryopreservation of hiPSCs was performed using a slow-freezing procedure with a Mr. Frosty™ Freezing Container filled with isopropyl alcohol (Sigma Aldrich), which has a cooling rate of approximately negative one degree Celsius per minute (−1° C. min$^{-1}$). The hiPSCs at eighty percent (80%) confluence were detached using Versene and suspended in pre-cooled cryopreservation solution. For the conventional method, the cryopreservation solution was made up often percent fetal bovine serum (10% FBS) and ten percent dimethyl sulfoxide (10% DMSO) in the mTeSR medium. The experimental cryopreservation solution contained 0-5% DMSO in the mTeSR medium with no FBS. All cryopreservation solutions and the Mr. Frosty™ Freezing Container were pre-cooled at four degrees Celsius (4° C.) for thirty minutes (30 mins) before use. The concentration of hiPSCs for cryopreservation was ten-million cells per milliliter (1×10$^7$ cells mL$^{-1}$) and each cryovial was loaded with two hundred fifty microliters (250 µL) of the cell suspension. Experimental conditions with sand-mediated ice seeding had one sand-PDMS film attached to the inside wall of the cryovial, with the sand surface being exposed to the cell suspension. The cryovials were loaded in the Mr. Frosty™ Freezing Container and stored in a negative eighty degrees Celsius (−80° C.) refrigerator overnight. Then, the cryovials with hiPSCs were transferred into the liquid nitrogen for long-term storage (e.g., two to five weeks).

To thaw the frozen samples with hiPSCs, two milliliters (2 mL) of mTeSR medium with a ten micromoles per liter (10 μM) ROCK inhibitor (RI, Y-27632, Sigma Aldrich) was added to each well (Matrigel coated) of a six-well plate and pre-warmed in the incubator at thirty-seven degrees Celsius (37° C.) for at least twenty minutes (20 min). The cryovial was removed from the liquid nitrogen tank and rapidly warmed in a thirty-seve degrees Celsius (37° C.) water bath for thirty seconds (30 s). The cell suspension in the cryovial was then transferred into the pre-warmed medium in the six-well plate for further incubation and studies. DMSO was not removed immediately after thawing to avoid centrifuging and washing the hiPSCs. The cells were cultured in the six-well plate with a medium containing a final DMSO concentration of 0.56% (250 μL cell suspension containing 5% DMSO diluted in 2 mL medium). After two hours (2 h), the DMSO-containing medium was replaced with a pre-warmed DMSO-free medium.

1.7. Live/Dead Assay and Cell Attachment Efficiency

To quantify their viability, the hiPSCs after thawing were cultured for two hours (2 h) and then stained with calcein AM and propidium iodide (PI) to visualize live (green with no red stain) and dead (red stain) cells, respectively. The two dyes were added into one milliliter (1 mL) of Dulbecco's Modified Eagle Medium/Nutrient Mixture F-12 ("DMEM/F12") (1 μM for calcein AM and 1 μg mL$^{-1}$ for PI) for incubating with the cells for five minutes (5 min) at thirty-seven degrees Celsius (37° C.). Afterward, green and red fluorescence images of the samples were taken using a Zeiss (Oberkochen, Germany) LSM710 microscope to count the live and dead cells. Cell viability is calculated as the percentage of live cells out of the total (i.e., live and dead) cells.

To quantify the cell attachment efficiency for studying the capability of the hiPSCs in attaching on culture dish, the mTeSR medium containing ROCK inhibitor was replaced with fresh mTeSR without ROCK inhibitor after two hours (2 h) of post-thawing incubation. After fifteen hours (15 h) of culture, the hiPSCs were detached and the cell number was counted. The cell attachment efficiency was calculated as the percentage of the cell number post-cryopreservation and fifteen hours (15 h) of culture out of the cell number cryopreserved in the cryovial.

1.8. Teratoma Assay

For the teratoma assay, hiPSCs at a confluence of eighty percent (80%) were detached and suspended at thirty million cells per milliliter (3×10$^7$ cells mL$^{-1}$) in one milliliter (1 mL) of a 1× concentration of phosphate-buffered saline (1×PBS) and then mixed with 500 μL of Matrigel (Corning). The cell suspension was kept on ice and then injected subcutaneously (s.c.) into the dorsal rear flank of non-obese diabetic/severe combined immunodeficiency mice (NOD.CB17-scid, Charles River, Frederick, MD, USA). Each mouse was injected with two hundred fifty microliters (250 μL) of the cell suspension and five mice (age: five weeks) were used for each experimental group. After five weeks, the mice were sacrificed and teratomas (n=5 for each group) were collected. The samples were fixed in four percent paraformaldehyde (4% PFA) in 1×PBS for two days. Afterwards, the samples were trimmed and embedded in paraffin for sectioning into slices of five micrometers (5 μm) in thickness. The slices were then stained with hematoxylin and eosin (H&E) and imaged with a Zeiss LSM710 microscope. All animal studies were approved by the Institutional Animal Care and Use Committee (IACUC) at the University of Maryland, College Park, MD 1.9 Neural and Cardiac Differentiation Neural differentiation was carried out by following previously reported protocols. Briefly, the hiPSCs were detached and suspended in mTeSR medium at 1×106 cells mL$^{-1}$. The samples were passed through a seventy microliter (70 μm) cell strainer (Gibco). The resultant hiPSC samples were cultured in mTeSR with a ten micromoles per liter (10 μM) ROCK inhibitor (Y-27632) for two days. Afterward, the medium was replaced with a neural differentiation medium and the cells were further cultured for ten days with the medium being changed every other day. The neural differentiation medium was a mixture of DMEM/F12 and neural basal medium (Gibco) (1:1 in volume) supplemented with 1× N2 (Gibco), 1× B27 (Gibco), one percent (1%) minimum essential medium non-essential amino acids (MEM NEAA, Gibco), and one percent (1%) L-glutamine (Invitrogen, Carlsbad, CA, USA). Lastly, the cells on day ten post-initiation of neural differentiation were fixed with four percent paraformaldehyde (4% PFA) for further immunostaining and analysis.

Cardiac differentiation was conducted also by following previous studies. The basal medium used for cardiac differentiation was a mixture of DMEM/F12 and alpha-Minimum Essential Medium (α-MEM) (ThermoFisher) (1:1 in volume) supplemented with two percent (2%) Knockout Serum Replacement (KOSR, Gibco), one micromole per liter (1 mM) L-glutamine, one percent (1%) MEM NEAA, and one-tenth micromoles per liter (0.1 mM) β-mercaptoethanol (Sigma Aldrich). For cardiac differentiation, hiPSCs were grown in a six-well plate coated with Matrigel. At eighty percent (80%) confluency, the hiPSCs were cultured with the mesoderm induction medium for two days. Then, the medium was replaced with the cardiac induction medium for the following eight days. Medium change was performed every other day. The mesoderm induction medium was made by supplementing five micromoles per liter (5 μM) CHIR99021 (ThermoFisher) and two micromoles per liter (2 μM) GSK inhibitor 6-bromoindirubin-3'-oxime (BIO, ThermoFisher) in the basal medium. The cardiac induction medium was made by supplementing ten micromoles per liter (10 μM) KY02111 (ThermoFisher) and ten micromoles per liter (10 μM) XAV939 (ThermoFisher) in the basal medium. Spontaneous beating areas in the sample were recorded using a Zeiss LSM710 microscope. The cells on day ten post cardiac differentiation were fixed with four percent paraformaldehyde (4% PFA) for further immunostaining and analysis.

1.10. Immunofluorescence Staining

For immunofluorescence staining, cells fixed with four percent paraformaldehyde (4% PFA) were gently rinsed twice with 1×PBS to remove the paraformaldehyde (PFA), permeabilized with one tenth percent (0.1%) TritonX-100 (Sigma Aldrich) in saline for ten minutes (10 min), incubated with one tenth percent (0.1%) Tween-20 (Sigma Aldrich) and five percent (5%) normal goat serum (Invitrogen) in saline for two hours (2 h) at room temperature (RT) to block non-specific binding. Afterwards, the samples were incubated with primary antibodies at four degrees Celsius (4° C.) overnight. The primary antibodies and their respective dilutions were as follows: for pluripotency, octamer-binding transcription factor 4 (OCT-4) (1:500 dilution, Cell Signaling Technologies, Danvers, MA, USA) and stage-specific embryonic antigen 4 (SSEA-4) (1:500 dilution, Cell Signaling Technologies); for cardiac differentiation, Cardiac Troponin T (cTnT) (1:500 dilution, Cell Signaling Technologies); for neural differentiation, Neuron-specific Class III β-tubulin (TUJ-1) (1:500; R&D Systems, Minneapolis, MN, USA). The secondary antibodies (goat anti-rabbit Immunoglobulin G (IgG) fluorescein isothiocyanate (FITC) and goat-anti-mouse Immunoglobulin G (IgG) phycoerythrin (PE), Invitrogen) at 1:1000 dilution was incubated with the samples for one- and one-half hours (1.5 h) at RT. Finally, the samples were rinsed with 1×PBS thrice and the nuclei were stained with 4',6-diamidino-2-phenylindole (DAPI) (1 µg mL$^{-1}$ in 1×PBS, Sigma Aldrich) for five min at RT before imaging with a Zeiss LSM710 microscope.

1.11. Protein Marker Expression

For flow cytometry studies of protein marker expression, cells were dissociated into single cells by incubating them with 0.25% trypsin (Gibco) for five minutes (5 min) at thirty-seven degrees Celsius (37° C.) and washed with 1×PBS twice. The dissociated cells were fixed with seventy-five percent (75%) ethanol at four degrees Celsius (4° C.) overnight. Then, the cells were permeabilized with 0.05% Triton X-100 for three minutes (3 min) and rinsed with 1×PBS twice. The cell number was adjusted to 1×106 cells per tube in seven hundred microliters (700 µL) of 1×PBS for each protein marker. The cells were incubated with primary antibodies including: OCT-4 (1:500 dilution, Cell Signaling Technologies), SSEA-4 (1:500 dilution, Cell Signaling Technologies) at four degrees Celsius (4° C.) overnight. Afterwards, the samples were rinsed with 1×PBS thrice before incubation with secondary antibodies (goat anti-mouse IgG FITC and goat anti-rabbit IgG PE, Invitrogen) at 1:1000 dilution for one hour (1 h) at RT. The samples were then washed with 1×PBS twice before analysis using a BD FACSCelesta (Franklin Lakes, NJ, USA) flow cytometer. The cells were incubated with secondary antibodies but no primary antibodies were processed and washed in the same way for analysis to serve as the negative/isotype control. The resultant data was analyzed with the BD Flowjo software (v10).

1.12. Cell Cycle Analysis

For cell cycle analysis, the cells fixed as aforementioned for protein marker expression studies were treated with RNase from bovine pancreas (1 µg mL-1, ThermoFisher) for five minutes (5 min) at RT. Then, the cells were stained with propidium iodide (PI) (1 µg mL$^{-1}$, ThermoFisher) for five minutes (5 min) at RT and rinsed with 1×PBS twice. Afterward, the cell concentration was adjusted to 1×106 cells per tube in seven hundred microliters (700 µL) of 1×PBS for analysis using a BD FACSCelesta flow cytometer. The resultant data was analyzed with the BD Flowjo software (v10).

1.13 Statistical Data Analysis

At least three independent runs on a different day were conducted for each experiment. All quantitative data were analyzed with Graphpad Prism (version 8, San Diego, CA, USA) and presented as mean±standard deviation. Student's t-test (two-tailed, unpaired, and assuming equal variance) was performed to assess the statistical significance of difference between two groups, and a difference with a p-value less than 0.05 was considered to be statistically significant.

2. Results 2.1 Fabrication and Characterization of Sand PDMS Film

Following the procedures outlined in FIGS. 1A and 6, sand-PDMS films were prepared for sticking on the inside wall in cryovials to seed ice and enhance the outcome of cryopreservation. The raw sands after cleaning (with water) and drying were gently sifted onto and partially embedded in a thin layer of uncured PDMS on top of a fully cured PDMS film using a mesh strainer with openings of two hundred micrometers (200 µm). After baking at seventy five degrees Celsius (75° C.) for thirty minutes (30 min) to crosslink the uncured PDMS, the resultant sand-PDMS films are cut into small pieces (3 mm×5 mm) and each piece is stuck via its smooth surface onto the inner wall of a cryovial for cryopreservation. The sand-PDMS film is soft and can be easily deformed onto the shape of the inner wall of cryovial for attaching to the wall via its smooth surface without any sand. No sands are observed to detach from the film when using the cryovial attached with the sand-PDMS film for cryopreservation studies, because the sands are partially embedded in the top PDMS layer to prevent them from detaching.

Before sifting, the sands are heterogeneous in size in nature as shown in FIG. 1B. After sifting with a 200 µm mesh strainer, the size of the resultant sand particles partially embedded in the PDMS film is significantly more homogenous than that before sifting and their sharp morphology is appreciable in the high-magnification image. Scanning electron microscopy (SEM) imaging of the sand-PDMS film shows that the sand protrudes out of the surface of the film, which is not seen on the plain PDMS surface of FIG. 1C. This is further confirmed by the energy dispersive X-ray spectroscopy (EDXS) data showing the higher occurrence of Silicon (Si) in the sand-PDMS film than the pure PDMS film, as shown in FIGS. 1D-1E.

2.2. Ice-Seeding With Sand-PDMS Film

The effect of sand on the ice-seeding temperature of water is investigated by measuring the change in temperature over time during cooling. Ice-seeding in the sample can be detected by a sudden temperature rise due to the release of latent heat of fusion as a result of ice nucleation and growth, as shown in FIG. 2A. Therefore, the temperature at which the sudden increase occurs is taken as the ice-seeding temperature. As shown in FIG. 2B, the ice-seeding temperature of water without any film (control) is −15.9±1.6° C. The addition of a pure PDMS film containing no sand in the cryovial causes no significant change in the ice-seeding temperature (−14.9±2.0° C.). When the sand-PDMS film is added into the cryovial, the ice-seeding temperature increases significantly to −7.8±1.6° C.

This capability of sands in seeding ice at the high subzero temperature is confirmed by the cryomicroscopy study of FIG. 2C to cool cryopreservation solution (mTeSR medium containing 5% DMSO) at a decrease of one degree Celsius per minute (−1° C./min). Initially, there is no evident ice formation at −9.2° C. in the cryopreservation solution (FIG. 2C, 0 s, first image in the series of images) because the solution around or away from the sand is transparent (the slightly darker appearance near the sand is probably due to the shadowing effect of the sand). After 0.5 s (second image in the series of images), the solution next to the sand becomes darkened (indicated by the white arrow) compared to the solution away from the sand, indicating the sand induces ice formation in the solution. Growth of ice into the solution away from the sand can be seen at 1.5 and 10 s (third and fourth images in the series of images, respectively: one of the ice growth fronts is indicated by a white arrow in the image for each of the two times), during which the temperature decreases from −9.2 to −9.4° C. This capability of sands in seeding ice in cryopreservation solution at a high subzero temperature can be useful for improving the outcome of cell cryopreservation, which is tested using hiPSCs.

2.3. Enhanced Cryopreservation of hiPSCs With Sand-Mediated Ice Seeding

To demonstrate the benefit of sand-mediated ice seeding for cryopreservation, hiPSCs are cryopreserved by slow-freezing under various conditions with or without the sand-mediated (by default) ice seeding: conventional method (10% DMSO and 10% FBS with no ice seeding), ice seeding alone, no cryoprotectant and no ice-seeding, 5% DMSO and no ice seeding, 2% DMSO and ice seeding, and 5% DMSO and ice seeding.

FIG. 3A shows typical live/dead images of the hiPSCs cryopreserved under the various conditions and cultured for two hours (2 h) at thirty-seven degrees Celsius (37° C.) after thawing, and the corresponding quantitative data of cell viability are shown in FIG. 3B. Without the use of any cryoprotectant, the sand-mediated ice seeding alone is insufficient to protect the cells from injury during the cryopreservation procedure, as indicated by the low cell viability under this condition (5.6±2.1%). This is only slightly higher than that for the condition with no cryoprotectant and no ice-seeding (1.3±0.6%). The use of 2% DMSO together with the sand-mediated ice seeding improved the hiPSC viability to 37.3±3.1%, showing the importance of using cryoprotectant to reduce cryoinjury to the cells. The cell viability is further improved albeit still modest for both the condition of 5% DMSO with no ice seeding condition (52.6±3.5%) and the conventional method using 10% DMSO and 10% FBS (51.7±4.0%). This demonstrates 5-10% DMSO could only protect up to ~50% hiPSCs from cryoinjury during cryopreservation and increasing DMSO from 5% to 10% does not significantly enhance the hiPSC viability in the absence of ice seeding. Importantly, high viability (90.3±2.5%) of the hiPSCs after cryopreservation can be achieved by combining the sand-mediated ice seeding with 5% DMSO. This viability is significantly higher than that of the other control groups.

Because the aforementioned immediate (2 h) cell viability judged by the live/dead staining assay is mainly a reflection of the cell membrane integrity, the cell viability (i.e., attachment efficiency) can be further determined by the percentage of cells that can attach after culturing for fifteen hour (15 h) post-thawing. FIG. 7 shows typical images of the cells after culturing for fifteen hour (15 h) post-thawing, and the corresponding quantitative data are shown in FIG. 3B. Overall, the hiPSC attachment efficiency is slightly lower than the cell viability assessed based on membrane integrity for all the conditions. Some cells with good membrane integrity judged by the live/dead assay may not be able to attach and survive in the long term. Furthermore, the hiPSC attachment efficiency follows the same trend as the immediate cell viability for the various conditions, and it is significantly and greatly higher for the condition of 5% DMSO and ice seeding than in all the other conditions.

Taken together, both the immediate (2 h) cell viability and long-term (15 h) cell viability (i.e., attachment efficiency) data show that 5% DMSO can be critical. However, further increasing DMSO may not be sufficient to protect hiPSCs from cryoinjury during cryopreservation. This can be resolved by combining 5% DMSO with the sand-mediated ice seeding to significantly and greatly enhance the outcome of hiPSC cryopreservation. Therefore, the hiPSCs cryopreserved by 5% DMSO and the sand-mediated ice seeding are further analyzed in terms of their pluripotency, cell cycle, and capability of differentiation to ascertain their long-term functional survival.

2.4. High Pluripotency and Normal Cell Cycle of Cryopreserved hiPSCs

The hiPSCs cryopreserved (cryo) using 5% DMSO and the sand-mediated ice seeding show typical colony morphology similar to that of fresh (control) hiPSCs under 2D monolayer culture, as shown in FIG. 4A. Furthermore, the cryopreserved hiPSCs are highly positive for pluripotency protein markers OCT-4 and SSEA-4, similar to that of the control group of fresh hiPSCs. Flow cytometry analyses are used to quantitatively evaluate the expression of pluripotency markers OCT-4 and SSEA-4. As shown in FIGS. 4B-4C, the cryopreserved hiPSCs highly express the two protein markers OCT-4 (96.7±2.3%) and SSEA-4 (96.1±1.6%), similar to the control fresh hiPSCs (97.2±1.4% positive on OCT-4 and 98.0±1.0% positive on SSEA-4) with no statistically significant difference. Moreover, the distribution of cryopreserved hiPSCs in the G1, S, and G2/M phases of cell cycle is similar to that of the control fresh cells with no statistically significant difference. Hence, the cryopreserved hiPSCs have similar proliferation capacity as the control fresh cells. In other words, these data show that the cryopreservation procedure with sand-mediated ice seeding and 5% DMSO has no evident impact on the pluripotency/stemness/self-renewal and the proliferation capacity of the hiPSCs.

2.5. Intact Capacity of Differentiation of the Cryopreserved hiPSCs

Figure 8A:
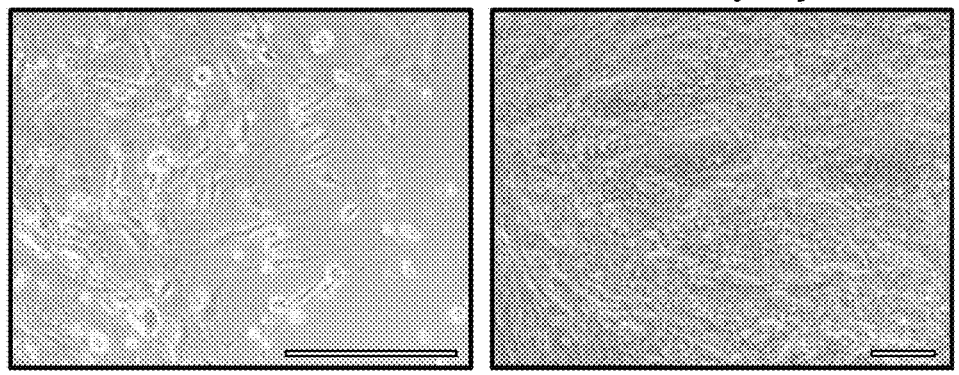
FIG. 8A shows fresh hiPSCs can differentiate into cells with typical neural cell morphology (neurites extending out of the cell body) after neural differentiation (left) and cells with typical morphology of cardiomyocytes (striated pattern).
Figure 8B:
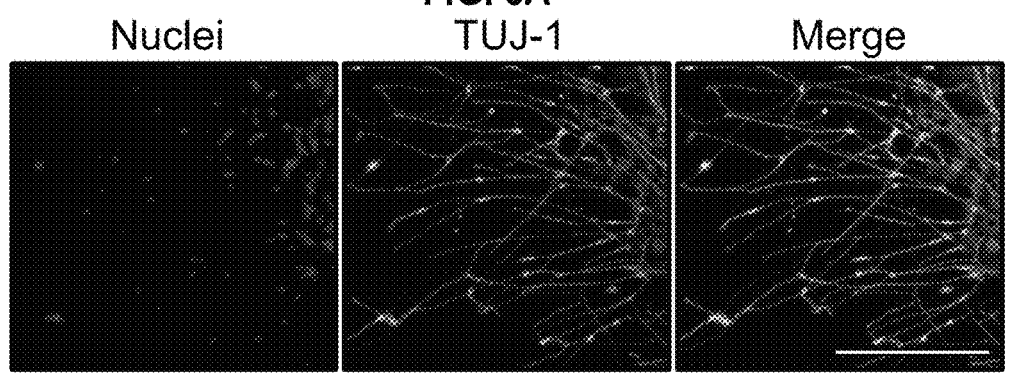
FIG. 8B evidences fresh control hiPSCs after neural differentiation show high expression of the neural specific protein marker TUJ-1. Images are captured wherein cell nuclei are made visible by DAPI staining.

To ascertain their functional survival, the cryopreserved hiPSCs are further assessed for their capacity of guided neural and cardiac differentiation in vitro and spontaneous teratoma formation in vivo. After ten days of neural differentiation, the cryopreserved hiPSCs lose their typical colony morphology and neurites are observable to extend out of the differentiated cells, as shown in FIG. 5A, similar to the fresh control cells of FIG. 8A. Furthermore, the resultant cells are positive for neural specific marker TUJ-1:95.9±1.5% of the cryopreserved hiPSCs post neural differentiation are positive for TUJ-1, similar to that (94.7±2.5%) of the fresh control hiPSCs, as shown in FIG. 8B.

Figure 8C:
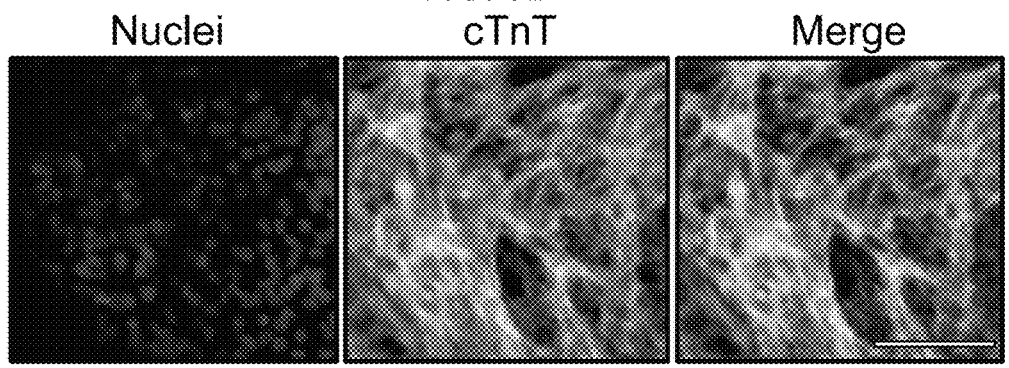
FIG. 8C evidences fresh control hiPSCs after cardiac differentiation highly express cardiac specific protein markers Cardiac muscle troponin T ("cTnT"). Images are captured wherein cell nuclei are made visible by DAPI staining.
Figure 8D:
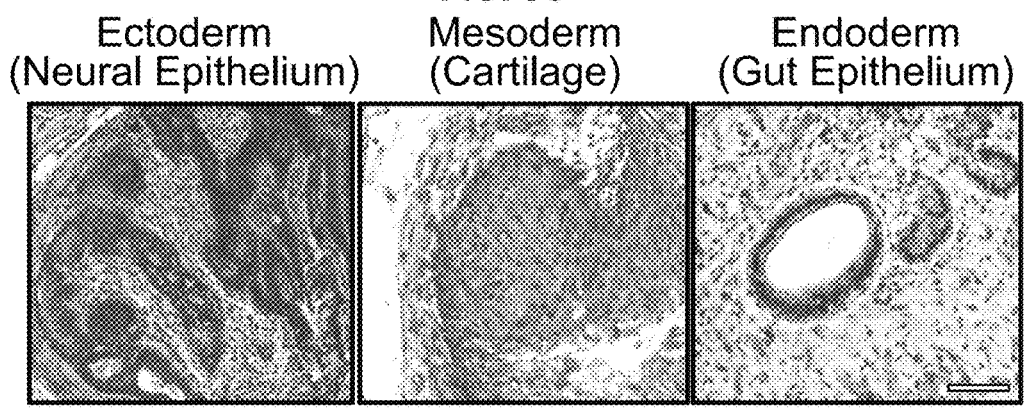
FIG. 8D shows teratomas grown from fresh hiPSCs contain tissues from all the three different germ layers including ectoderm (neural epithelium with hypernucleated neuroectodermal structures), mesoderm (the nidus of cartilage with surrounding condensed mesenchymal cells), and endoderm (gut epithelium with subnuclear vacuoles and tube-like structure).

The data demonstrate the cryopreserved hiPSCs maintain their capacity of neural differentiation. The capability of cardiac differentiation of the cryopreserved hiPSCs is also evidenced by the spontaneously beating areas observable in ten days after initiation of the differentiation, similar to the areas seen in the fresh control cells. The percentage of cells on day ten day positive for the cardiac specific marker cTnT is not significantly different between the cryo (87.9±2.6%) and fresh control (85.6±4.8%) groups, as shown in FIG. 5B. The cardiac muscle-like striated pattern can be seen on both the cTnT-stained fluorescence images and the non-fluorescence images showing the cell morphology of both cryopreserved, as shown in FIG. 5B, and fresh control, as shown in FIGS. 8A&8C, hiPSCs-derived cardiomyocytes. Lastly, the cryopreserved hiPSCs maintain the capability of teratoma formation in vivo. The teratomas of FIG. 5C were grown from the cryopreserved hiPSCs show typical tissue structure of the three germ layers: the neural epithelium of ectoderm with hypernucelated neuroectodermal structures, cartilage of mesoderm showing the nidus of cartilage with surrounding condensed mesenchymal cells, and gut epithelium of endoderm with subnuclear vacuoles and tube-like structure. Similar tissue structures are observable in the teratomas of the fresh control group of FIG. 8D. All these data on neural and cardiac differentiation in vitro and teratoma formation in vivo for the cryopreserved hiPSCs is similar to the that for the fresh hiPSCs with no cryopreservation, showing cryopreservation with 5% DMSO and the sand-mediated ice-seeding have no evident impact on the differentiation capacity of the hiPSCs.

From the foregoing, it can be seen that the present disclosure accomplishes at least all of the stated objectives.

LIST OF REFERENCE CHARACTERS

The following table of reference characters and descriptors are not exhaustive, nor limiting, and include reasonable equivalents. If possible, elements identified by a reference character below and/or those elements which are near ubiquitous within the art can replace or supplement any element identified by another reference character.

TABLE 1

| List of Reference Characters | |
|---|---|
| 100 | sands |
| 101 | glass slide |
| 102 | PDMS film |
| 103 | uncured PDMS layer |
| 104 | pre-heating step |
| 106 | sand-PDMS film |
| 107 | flat surface |
| 108 | cryovial(s) |
| 109 | base |
| 110 | inner surface |
| 112 | sand-PDMS surface |
| 114 | PDMS surface |
| 116 | plastic shard-PDMS surface |
| 118 | glass bead-PDMS surface |

Glossary

Unless defined otherwise, all technical and scientific terms used above have the same meaning as commonly understood by one skilled in the art to which embodiments of the present disclosure pertain.

The terms "a," "an," and "the" include both singular and plural referents.

The term "or" is synonymous with "and/or" and means any one member or combination of members of a particular list.

The term "about" as used herein refers to slight variations in numerical quantities with respect to any quantifiable variable. Inadvertent error can occur, for example, through the use of typical measuring techniques or equipment or from differences in the manufacture, source, or purity of components.

The term "substantially" refers to a great or significant extent. "Substantially" can thus refer to a plurality, majority, and/or a supermajority of the quantifiable variable(s), given the proper context.

The term "generally" encompasses both "about" and "substantially."

The term "configured" describes structure capable of performing a task or adopting a particular configuration. The term "configured" can be used interchangeably with other similar phrases, such as constructed, arranged, adapted, manufactured, and the like.

Terms characterizing sequential order, a position, and/or an orientation are not limiting and are only referenced according to the views presented.

The term "seed" when used as a verb herein, means to introduce ice crystals into an undercooled sample.

The "scope" of the present disclosure is defined by the appended claims, along with the full scope of equivalents to which such claims are entitled. The scope of the present disclosure is further qualified as including any possible modification to any of the aspects and/or embodiments disclosed herein which would result in other embodiments, combinations, subcombinations, or the like that would be obvious to those skilled in the art.

What is claimed is:

1. A method of cell/tissue cryopreservation comprising:
   immobilizing a silicon dioxide ($SiO_2$) based sand on a polydimethylsiloxane (PDMS) film to form a sand-PDMS film, wherein the $SiO_2$ based sand is non-toxic and partially embedded in the PDMS film such that at least a portion of sand surface is exposed, adhering the sand-PDMS film to a portion of an inner plastic surface of a container;
   suspending the cells/tissues in a solution within the container with the sand surface being exposed to the cell/tissue suspension, wherein the sand-PDMS film prevents the $SiO_2$ based sand from mixing with the solution; and
   cooling the solution to a temperature at least negative twenty degrees Celsius (−20° C.), wherein the sand-PDMS film seeds ice into the solution at a temperature warmer than negative fifteen degrees Celsius (−15° C.).

2. The method of claim 1, wherein the method is free from vitrification and/or use of a serum.

3. The method of claim 1, further comprising using a serum.

4. The method of claim 1, further comprising a cryoprotectant at a concentration of no more than 15%.

5. The method of claim 1, wherein the cells/tissues are human induced pluripotent stem cells (hiPSCs).

6. The method of claim 1, further comprising storing the cells/tissues in a frozen state.

7. The method of claim 6, further comprising thawing the cells/tissues with a survival rate of at least seventy percent (70%).

8. The method of claim 7, wherein the cells/tissues are human induced pluripotent stem cells (hiPSCs) and wherein the method further comprises retaining (i) pluripotency in the hiPSCs after thawing the hiPSCs and (ii) a capability of the hiPSCs to differentiate into the three germ layers.

9. The method of claim 7, further comprising, after thawing, practicing and/or researching cell-based translational medicine with the thawed cells/tissues.

10. The method of claim 1, wherein the cells/tissues are selected from the group consisting of stem cells, immune cells, single somatic cells, somatic cell aggregates, pancreatic islets and ovarian follicles.

11. The method of claim 1, wherein the sand-PDMS film comprises a cured combination of the $SiO_2$ based sand, a PDMS prepolymer, and a curing agent.

12. The method of claim 11, wherein the PDMS prepolymer and the curing agent form a layer having a thickness between one hundredth millimeters (0.01 mm) and one hundred millimeters (100 mm).

13. The method of claim 11, wherein the PDMS prepolymer and the curing agent form a layer having a thickness between one tenth millimeters (0.1 mm) and ten millimeters (10 mm).

14. The method of claim 11, wherein the PDMS prepolymer and the curing agent form a layer having a thickness between one half millimeters (0.5 mm) and one and one half millimeters (1.5 mm).

15. The method of claim 1, wherein the container is a cryovial having at least one opening and wherein the container further comprises a removable cap or plug for opening and closing the at least one opening.

16. The method of claim 15, wherein the cryovial further comprises a base for supporting the cryovial such that the cryovial can rest upright on a flat surface without tipping or rolling.

17. The method of claim 1, wherein the sand-PDMS film seeds ice into the solution at a temperature warmer than negative ten degrees Celsius (−10° C.).

* * * * *